United States Patent
Jung et al.

(10) Patent No.: US 9,561,303 B2
(45) Date of Patent: *Feb. 7, 2017

(54) CONTROLLING CALCIUM COMPOUND FORMATION IN BIOCOMPATIBLE MATERIALS FOR TISSUE REGENERATION AND REPAIR IN MAMMALS

(75) Inventors: Steven B. Jung, Rolla, MO (US);
Delbert E. Day, Rolla, MO (US)

(73) Assignee: The Curators of the University of Missouri, Columbia, MO (US)

( * ) Notice: Subject to any disclaimer, the term of this patent is extended or adjusted under 35 U.S.C. 154(b) by 454 days.

This patent is subject to a terminal disclaimer.

(21) Appl. No.: 13/543,115

(22) Filed: Jul. 6, 2012

(65) Prior Publication Data
US 2012/0276218 A1   Nov. 1, 2012

Related U.S. Application Data

(63) Continuation-in-part of application No. PCT/US2010/048778, filed on Sep. 14, 2010, which (Continued)

(51) Int. Cl.
*A61K 33/22* (2006.01)
*A61K 33/34* (2006.01)
(Continued)

(52) U.S. Cl.
CPC .............. *A61L 27/10* (2013.01); *A61L 27/58* (2013.01); *A61F 2/0077* (2013.01)

(58) Field of Classification Search
CPC .......... A61L 27/58; A61L 27/10; A61F 2/0077
(Continued)

(56) References Cited

U.S. PATENT DOCUMENTS 4,243,567 A * 1/1981 Potter .......................... 524/405
4,250,277 A * 2/1981 Maries et al. ............... 525/337
(Continued)

FOREIGN PATENT DOCUMENTS

GB        2037735           7/1980
WO   WO 2007144662 A1 * 12/2007 ............. A61L 27/10
WO   WO 2011084192 A1 *  7/2011 ............. A61L 27/10

OTHER PUBLICATIONS

Helbig et al. (DE 10 2004 021 700 A1; machine translation from European Patent Office (EPO) provided by USPTO STIC translation services (Jun. 24, 2014), 9 pages).*

(Continued)

*Primary Examiner* — Anna Pagonakis
*Assistant Examiner* — Miriam A Levin
(74) *Attorney, Agent, or Firm* — Senniger Powers LLP

(57) ABSTRACT

A biocompatible composition for tissue repair or regeneration in mammals comprising one or more glass former compounds selected from the group consisting of $B_2O_3$, $P_2O_5$, and $SiO_2$ and director elements selected from the group consisting of Cu, Sr, Zn, Fe, Mn, Cr, V, Nb, Mo, W, Ba, Co, S, Al, Ti, Y, Mg, Si and/or Ni to promote in vivo calcium compound formation of calcium carbonate or other calcium compounds other than hydroxyapatite. Upon direct application of the biocompatible composition to a mammalian host, calcium carbonate or other calcium compounds other than hydroxyapatite form upon bioreaction of the composition with bodily fluids.

21 Claims, 20 Drawing Sheets

Related U.S. Application Data is a continuation of application No. 12/683,280, filed on Jan. 6, 2010, now Pat. No. 8,287,896.

(51) Int. Cl.

| | |
|---|---|
| *A61K 33/24* | (2006.01) |
| *A61K 33/32* | (2006.01) |
| *A61K 33/30* | (2006.01) |
| *A61K 33/20* | (2006.01) |
| *A61L 27/10* | (2006.01) |
| *A61L 27/58* | (2006.01) |
| *A61F 2/00* | (2006.01) |

(58) Field of Classification Search
USPC .............. 424/630, 617, 639, 641, 646, 660
See application file for complete search history.

(56) References Cited

U.S. PATENT DOCUMENTS

| | | | |
|---|---|---|---|
| 5,204,106 A | 4/1993 | Schepers et al. | |
| 6,709,744 B1* | 3/2004 | Day et al. | 428/403 |
| 8,173,154 B2* | 5/2012 | Jung | A61F 13/00008 |
| | | | 424/445 |
| 8,287,896 B2* | 10/2012 | Jung | A61L 27/58 |
| | | | 424/423 |
| 8,337,875 B2* | 12/2012 | Jung et al. | 424/423 |
| 8,481,066 B2* | 7/2013 | Day et al. | 424/423 |
| 8,535,710 B2* | 9/2013 | Jung | A61F 13/00008 |
| | | | 424/443 |
| 8,821,919 B2* | 9/2014 | Jung | A61K 33/22 |
| | | | 424/400 |
| 2002/0160175 A1 | 10/2002 | Pirhonen | |
| 2004/0170692 A1 | 9/2004 | Day et al. | |
| 2005/0013873 A1* | 1/2005 | Fechner et al. | 424/601 |
| 2008/0044488 A1* | 2/2008 | Zimmer et al. | 424/600 |
| 2008/0066495 A1 | 3/2008 | Moimas et al. | |
| 2009/0208428 A1 | 8/2009 | Hill et al. | |
| 2009/0276056 A1* | 11/2009 | Bose | A61L 27/12 |
| | | | 623/23.72 |
| 2011/0014261 A1* | 1/2011 | Day | A61L 27/10 |
| | | | 424/423 |
| 2011/0014262 A1* | 1/2011 | Jung | A61L 27/10 |
| | | | 424/423 |
| 2011/0165217 A1 | 7/2011 | Jung et al. | |

OTHER PUBLICATIONS

Liang et al., Bioactive borate glass scaffold for bone tissue engineering, Journal of Non-Crystalline Solids (2008), 354: 1690-1696.*

International Preliminary Report on patentability for PCT/US2010/041854 (Jan. 17, 2012), 7 pages.*

International Search Report for PCT/US2010/041854 (Sep. 14, 2010), 3 pages.*

"A New Generation of Bioactive Materials Useful for Bone and Tissue Repair", Missouri University of Science and Technology [online], Sep. 13, 2010, <http://www.ibridgenetwork.org/file_records/show/8512>.

Li et al., "An investigation of bioactive glass powders by sol-gel processing", Journal of Applied Biomaterials, 1991, vol. 2, Issue 4, pp. 231-239, Abstract only, 1 page.

International Search Report, PCT/2010/48778, dated Oct. 26, 2010, 4 pages.

Written Opinion, PCT/2010/848778, dated Oct. 26, 2010, 6 pages.

Neel et al., "Characterisation of antibacterial copper releasing degradable phosphate glass fiber", Biomaterials 26 (2005) 2247-2254).

Richard et al., "Bioactive Behavior of Borate Glass", A Thesis, University of Missouri—Rolla, Apr. 2000, 139 pages.

Mir et al., "Adequate Serum Copper Concentration Could Improve Bone Density, Postpone Bone Loss and Protect Osteoporosis in Women", Iranian J. Publ. Health, 2007, A supplementary issue on Osteoporosis, pp. 24-29.

Priest N. D., Van De Vyver, F. L., Trace Metals and Fluoride in Bones and Teeth, pp. 232-237, 254-258, CRC Press, Boca Raton FL. (1990).

Beattie, J. H., Avenell, A., Trace Element Nutrition and Bone Metabolism, Nutrition Research Reviews (1992), 5, 167-188.

Nielsen, F. H., Nutritional Requirements for Boron, Silicon, Vanadium, Nickel, and Arsenic: Current Knowledge and Speculation, The FASEB Journal, 5, (1991) 2661-2667.

Schroeder, H. A., Nason, A. P., Trace Element Analysis in Clinical Chemistry, Clinical Chemistry, 17, 6, (1971).

Ning, Jia et al., "Synthesis and in Vitro Bioactivity of a Borate-Based Bioglass", Materials Letters, vol. 61, Issue 30, Dec. 2007, pp. 5223-5226.

Liang, Wen, "Bioactive Comparison of a Borate, Phosphate and Silicate Glass", Journal of Materials Research, vol. 21, Issue 1, 2005, pp. 125-131.

Yao, Aihua et al., "In Vitro Bioactive Characteristics of Borate-Based Glasses with Controllable Degradation Behavior", Journal of the American Ceramic Society, vol. 90 Issue 1, Nov. 7, 2006, pp. 303-306.

Gorustovich et al., "Biological performance of boron-modified bioactive glass particles implanted in rat tibia bone marrow", Biomedical Materials, vol. 1, 2006, pp. 100-105.

Rahaman et al., "Bioactive Glasses for Nonbearing Applications in Total Joint Replacement", Seminars in Arthroplasty, vol. 17, Issues 3-4, Sep.-Dec. 2006, pp. 102-112.

Haimi et al., "Characterization of zinc-releasing three-dimensional bioactive glass scaffolds and their effects on human adipose stem cell proliferation and osteogenic differentiation", Acta Biomater. 5, 2009, pp. 3122-3131.

* cited by examiner

CONTROLLING CALCIUM COMPOUND FORMATION IN BIOCOMPATIBLE MATERIALS FOR TISSUE REGENERATION AND REPAIR IN MAMMALS

REFERENCE TO RELATED APPLICATION

This application is a continuation-in-part application of PCT/US2010/048778 published as WO 2011/084192 and filed on Sep. 14, 2010, claiming priority to U.S. application Ser. No. 12/683,280 filed Jan. 6, 2010, the entire disclosures of which are incorporated herein by reference.

STATEMENT OF GOVERNMENT INTEREST

This invention was made with Government support under Department of the Army contract W81XWH-08-1-7065. The Government may have certain rights in the invention.

FIELD OF THE INVENTION

This invention relates to biocompatible compositions for surface and subsurface implantation into mammals to facilitate tissue repair, regeneration, and proliferation.

BACKGROUND OF THE INVENTION

Bioactive glasses have been known for nearly 40 years and are considered osteoinductive and osteoconductive. They are currently used in a variety of bone repair and regeneration applications since these glasses react in a favorable way with the bodily fluids to form a calcium phosphate compound known as hydroxyapatite (HA) or carbonated hydroxyapatite (HCA). Since HA or HCA is the mineral component of natural bone, bioactive glasses form a strong chemical bond to human bone and over a period of time they are considered to be remodeled by the body to form new bone.

Silicate-based glasses have been used as a basis for implantable compositions to support the bonding, growth or genesis of bone by fostering a supportive environment between the material and living, bone progenitor cells. It is widely recognized that successful bioactive glasses include calcium and silica in order to foster the needed supportive environment. Certain of these compositions are considered bioactive since they possess surfaces capable of fostering a calcium phosphate layer which, in turn, promotes bone bonding to the material. For example, U.S. Pat. No. 5,204,106 discloses a composition termed 45S5 glass which is composed of $Na_2O$—$CaO$—$P_2O_5$—$SiO_2$.

Day et al. U.S. Pat. No. 6,709,744 describes biocompatible materials for implantation which include borate-based glass or ceramic materials containing $Na_2O$, $CaO$, $P_2O_5$, and $B_2O_3$. A specific example is a glass containing about 22.9 wt % $Na_2O$, about 22.9 wt % $CaO$, about 5.6 wt % $P_2O_5$, and about 48.6 wt % $B_2O_3$. These materials contain a high CaO concentration to facilitate the formation of hydroxyapatite when exposed to phosphorus-containing fluids in vivo or prior to implantation.

There is a continuing need for a wider variety of biocompatible materials which promote rapid repair of mammalian tissue.

SUMMARY OF THE INVENTION

Briefly, therefore, the invention is directed to the repair and regeneration of both soft and hard tissue (bones) in a time frame which is more rapid than is currently possible with bioactive silicate glasses and wherein the bioactive glasses react with the bodily fluids to form not only hydroxyapatite but also other calcium containing compounds which are biologically more preferred than the hydroxyapatite reaction product formed by the reaction of silicate glasses, and in certain applications to form such other calcium containing compounds and affirmatively avoid forming hydroxyapatite.

In another aspect, the invention is directed to a biocompatible composition for tissue repair or regeneration in mammals comprising one or more glass former compounds selected from the group consisting of $B_2O_3$, $P_2O_5$, and $SiO_2$; director elements selected from the group consisting of Cu, Sr, Zn, Fe, Mn, Cr, V, Nb, Mo, W, Ba, Co, S, Al, Ti, Y, Mg, Si and/or Ni to promote in vivo calcium compound formation of calcium carbonate or other calcium compounds other than hydroxyapatite or amorphous calcium-containing materials other than hydroxyapatite; wherein upon direct application of the biocompatible composition to a mammalian host, calcium carbonate or other calcium compounds other than hydroxyapatite or amorphous calcium-containing materials other than hydroxyapatite form upon bioreaction of the composition with bodily fluids.

The invention is also directed to use of a composition comprising one or more glass former compounds selected from the group consisting of $B_2O_3$, $P_2O_5$, and $SiO_2$ and director elements selected from the group consisting of Cu, Sr, Zn, Fe, Mn, Cr, V, Nb, Mo, W, Ba, Co, S, Al, Ti, Y, Mg, Si and/or Ni to promote in vivo calcium compound formation of calcium carbonate or other calcium compounds other than hydroxyapatite or amorphous calcium-containing materials other than hydroxyapatite.

In another aspect, the invention is directed to a method for forming a calcium compound in vivo in a mammal comprising implanting into the mammal a composition comprising one or more glass former compounds selected from the group consisting of $B_2O_3$, $P_2O_5$, and $SiO_2$ and director elements selected from the group consisting of Cu, Sr, Zn, Fe, Mn, Cr, V, Nb, Mo, W, Ba, Co, S, Al, Ti, Y, Mg, Si and/or Ni to promote in vivo calcium compound formation of calcium carbonate or other calcium compounds other than hydroxyapatite or amorphous calcium-containing materials other than hydroxyapatite.

Other objects and features of the invention are in part apparent and in part pointed out hereinafter.

DESCRIPTION OF PREFERRED EMBODIMENTS

Figure 1A:
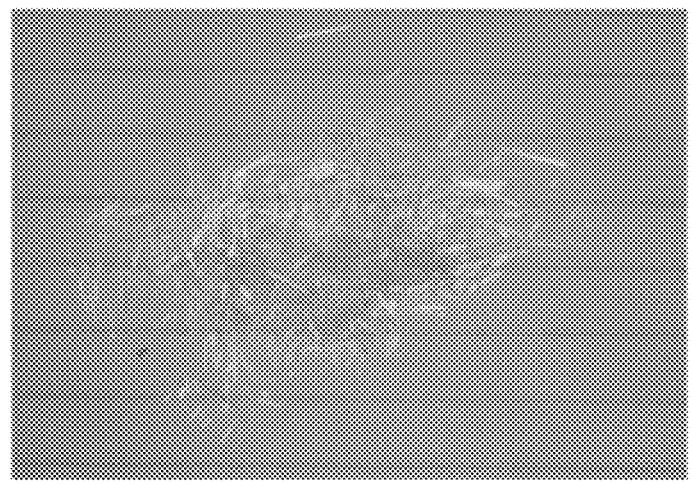
FIG. 1A shows chopped fibers 2 to 3 mm in length, 100 to 300 μm in diameter, used for making compositions of the invention.

The compositions of the invention employ one, two, or all three of $B_2O_3$, $SiO_2$, or $P_2O_5$ as glass former compounds. The compositions contain calcium and one or more elements which direct the formation of calcium-containing compounds other than hydroxyapatite upon biodegradation of the compositions in vivo. The compositions are in the form of particulates, scaffold, mesh, or other form which is implantable or a form such as mesh or wrap which can be applied to the skin. The below discussion focuses on implantation of the composition into a mammalian host; but in all significant aspects the invention is equally suitable for other forms of direct application to the mammalian host such as a mesh or wrap applied over the skin. In other words, the invention is applicable to both surface and subsurface application, provided the composition is exposed to the mammalian host's bodily fluids.

All known bioactive glasses such as the well known 45S5 and 13-93 react with the bodily fluids to form a hydroxyapatite type material. The term "bioactive" has come to refer specifically to materials which react with bodily fluids to form a calcium phosphate material such as hydroxyapatite, non-stoichiometric hydroxyapatite, amorphous hydroxyapatite, or carbonated hydroxyapatite. As used herein, the term "hydroxyapatite" designates these materials collectively unless stated otherwise. And while these are desirable materials for many in vivo applications because, for example, HA mimics bone, there are applications where it is desirable to form other types of calcium-containing materials when a bioactive glass reacts with bodily fluids. And there are applications where it is desirable to avoid the formation of hydroxyapatite materials. In accordance with this invention, the type of calcium-containing materials which forms when a bioactive glass reacts in vivo is controlled and directed, so that in some embodiments calcium-containing materials are formed in addition to HA, and in other embodiments calcium-containing materials are formed instead of HA. This discovery offers the possibility of expanding the uses of bioactive glasses for bone replacement/repair applications and creating bioactive glasses which can react faster in the body and can convert to new bone more quickly than the presently available bioactive glasses. To distinguish from "bioactive" and "bioactivity" which have come to refer to HA formation, this application uses the terms "bioreactive" and "bioreactivity" to refer to reaction of the glass materials to form calcium-containing compounds which are not hydroxyapatite.

A material that reacts with the bodily fluids to form calcite is resorbed by the body faster than a material that reacts to form hydroxyapatite (HA), especially stoichiometric crystalline HA. The solubility of hydroxyapatite is 5 mg/L at pH 7.3, whereas the solubility of calcite is 6.6 mg/L. Calcite has also been found to be osteogenic (promotes bone growth), and when compared to hydroxyapatite is more effective in promoting bone growth. Therefore, a glass that forms calcium carbonate, especially in the form of calcite—the most stable polymorph of calcium carbonate $CaCO_3$—is expected to be resorbed faster by the body than a glass that forms hydroxyapatite $(Ca_{10}(PO_4)_6(OH)_2)$. Because calcium carbonate is also osteogenic in that it promotes new bone formation, it promotes faster complete healing of bony defects. Calcium compounds other than hydroxyapatite include, for example, calcite, vaterite $(CaCO_3)$, calcium fluoride $(CaF_2)$ tricalcium phosphate $(TCP)(Ca_3(PO_4)_2)$, tetracalcium phosphate $(Ca_4(PO_4)_2O)$, oxyapatite, octacalcium phosphate $(OCP)(Ca_8H_2(PO_4)_6\text{-}5H_2O$, monetite $(DCPA)(CaHPO_4)$, brushite $(DCPD)(CaHPO_4\text{-}2H_2O)$, and calcium hydroxide $(Ca(OH)_2$. In some instances intermediate products which one might consider to not be compounds per se will form; so in this respect the invention involves forming calcium-containing materials (i.e., not necessarily compounds), which are not hydroxyapatite. In a particular system some of these may be metastable and transition compounds. From solubility data for many of these compounds, one would be expected hydroxyapatite to precipitate early, because of its low solubility, relative to these other compounds, upon introduction of Ca into a system containing P, O, H, and C, such as bodily fluids:

TABLE 1

| Material | Chemical Formula | Solubility (mg/L) |
|---|---|---|
| Hydroxyapatite (HA) | $Ca_{10}(PO_4)_6(OH)_2$ | 5* |
| Calcite | $CaCO_3$ | 6.6 |
| Vaterite | $CaCO_3$ | 11 |
| Calcium Fluoride | $CaF_2$ | 16 |
| Tricalcium Phosphate (TCP) | $Ca_3(PO_4)_2$ | 33* |
| Octacalcium Phosphate (OCP) | $Ca_8H_2(PO_4)_6$—$5H_2O$ | 39* |
| Monetite (DCPA) | $CaHPO_4$ | 135* |
| Brushite (DCPD) | $CaHPO_4$—$2H_2O$ | 194* |
| Calcium Hydroxide | $Ca(OH)_2$ | 1600 |

1Hydroxyapatite and Related Materials, Brown and Constantz, 1994
2Handbook of Chemistry and Physics (90th edition) 2009-2010
*Denotes a value calculated from solubility isotherms from FIG. 1 on page 74, pH = 7.3

So if a source of calcium such as a Ca-containing biodegradable glass is implanted into an environment of P, O, and C, one would expect, as the Ca ions are released, to form hydroxyapatite sooner than calcite. However, if HA can be prevented from forming then the next least soluble phase, calcite, would be expected to form. One would also expect these other compounds, if present in a particular system such as bodily fluids, would dissociate into Ca, P etc. ions relatively sooner than hydroxyapatite. Furthermore, if calcite dissociates into its ions sooner than does hydroxyapatite, then such ions are available to perform a desired function in the body sooner. That function in the instance of bone repair is to grow hydroxyapatite at damaged bone sites. In other words, calcite facilitates growth of remodeled hydroxyapatite on a bone substrate more quickly than hydroxyapatite does. It may therefore be advantageous for a bone repair implant to, upon implantation, form calcite instead of or in addition to hydroxyapatite. This invention leverages this concept by including director elements which essentially alter the normal hierarchy of calcium compound formation one would expect from the above solubility data as well as from the accepted maxim in the field that calcium-containing glasses in physiological fluids form hydroxyapatite. That is, the glass compositions of this invention are specifically formulated to biodegrade in physiological fluids to form calcite and/or other calcium-containing compounds instead of, or in addition to, hydroxyapatite.

In accordance with this invention, the elements which direct the formation of calcium-containing compounds other than hydroxyapatite upon biodegradation of the compositions in vivo constitute minor amounts of Cu, Sr, Zn, Fe, Mn, Cr, V, Nb, Mo, W, Ba, Co, S, Al, Ti, Y, Mg, Si and/or Ni which are employed as a so-called "director elements" to control the formation of HA and bias the in vivo calcium compound formation toward calcium carbonate or other calcium compounds other than hydroxyapatite or amorphous calcium-containing materials other than hydroxyapatite. In one embodiment, the director element is Cu, Zn, Fe, Mn, Ba, Co, S, V, and/or Y either individually or in combination; and in one preferred embodiment, the director element is Cu, Zn, Fe, Mn, Ba, Co, and/or S; such as in one more particularly preferred embodiment where the director element is Zn and/or Fe, or one or more of Cu, Mn, Ba, Co, and/or S. Wherever this description refers to "director element" in the singular, it is to be understood to encompass one director element or two or more of the director elements. The invention in one aspect therefore involves use of a composition to promote in vivo calcium formation of calcium carbonate or other calcium compounds other than hydroxyapatite or amorphous calcium-containing materials other than hydroxyapatite, wherein the composition comprises one or more glass former compounds selected from the group consisting of $B_2O_3$, $P_2O_5$, and $SiO_2$; and director elements selected from the group consisting of Cu, Sr, Zn, Fe, Mn, Cr, V, Nb, Mo, W, Ba, Co, S, Al, Ti, Y, Mg, Si and/or Ni. As is evident from the following description, the invention includes a method for forming a calcium compound in vivo in a mammal comprising implanting into the mammal a composition comprising one or more glass former compounds selected from the group consisting of $B_2O_3$, $P_2O_5$, and $SiO_2$ and director elements selected from the group consisting of Cu, Sr, Zn, Fe, Mn, Cr, V, Nb, Mo, W, Ba, Co, S, Al, Ti, Y, Mg, Si and/or Ni to promote in vivo calcium compound formation of calcium carbonate or other calcium compounds or amorphous calcium-containing materials other than hydroxyapatite.

Calcium-containing implantable bioactive glasses form hydroxyapatite upon reaction with bodily fluids according to the following ideal reaction:

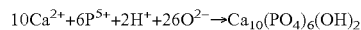

$$10Ca^{2+}+6P^{5+}+2H^{+}+26O^{2-} \rightarrow Ca_{10}(PO_4)_6(OH)_2$$

In accordance with this invention, the glass composition is formulated to include the one or more director elements so as to produce desired calcium compounds or amorphous calcium-containing materials other than hydroxyapatite. In some embodiments, these other calcium compounds and/or materials are formed entirely instead of hydroxyapatite. In other embodiments, a mixture of hydroxyapatite and one or more other calcium-based compounds is formed. In one preferred embodiment of the invention, the implantable glass composition is formulated to promote the formation of calcite upon reaction with bodily fluids in vivo. The major calcite formation reaction is as follows:

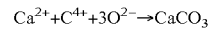

$$Ca^{2+}+C^{4+}+3O^{2-} \rightarrow CaCO_3$$

Without being bound to a particular theory, it appears the atomic/ionic radius of a particular element has an impact on its efficacy as a director element alone or in combination with other elements in accordance with this invention. In particular, it is believed that an element with a relatively smaller ionic radius such as less than about 1 angstrom, or on the order of 0.8 angstroms or less, provides moderate to severe inhibition of hydroxyapatite formation, and biases the system toward calcite formation.

The invention is useful in a wide variety of implantable applications and other tissue regenerative applications. Herein it will be described in the context of an implantable scaffold. In accordance with this invention, a director element is incorporated into, for example, a scaffold of a biocompatible composition which is implantable at a mammal's surface or subsurface. The scaffold composition may optionally provide ions for biological use by the mammal, as described in co-pending application Ser. No. 12/683,280, the entire disclosure of which is incorporated by reference. The elements which function as director elements may also have other benefits, or separate trace elements may be incorporated as described in the co-pending application, independent of the elements' ability to function as director elements in accordance with this invention. These elements have beneficial effects such as an effect on endothelial cell migration which can be useful for blood vessel formation and have importance for tissue regeneration. In this way, these elements promote angiogenesis, which is a critical function in promoting tissue growth, such as in wound healing. This is in distinction from promoting osteoconductivity, which refers to providing bone growth factors to a site to promote bone growth. Angiogenesis, which involves increasing vascularity, i.e., vessel growth, is distinct from osteoconductivity. However, certain of these director elements assist in promoting osteoconductivity as well.

The scaffold of the invention comprises a scaffold body comprising a biocompatible material in the form of one or more of fibers, hollow fibers, tubes, ribbons, solid spheres, hollow spheres, particles, bonded particles, and combinations thereof. In many of the more preferred embodiments, the form is loose or bonded fibers, or bonded particles. Generally speaking, a scaffold composed of multiple fibers and/or other of these elements has a weight of at least about 10 milligrams, such as between about 10 milligrams and about 500 grams, for example between about 20 milligrams and about 2500 milligrams. The scaffold weight/dimensions depend upon the size of the wound/space being treated. The biocompatible material is borate-based, phosphate-based, and/or silicate-based and is glass, crystalline, or a combination of glass and crystalline.

The biocompatible material fibers, spheres, or other-shaped components in some embodiments are in a loose assembly of nonbonded components. Alternatively, they are bonded to each other, typically by heating, to define a scaffold body and provide a scaffold body compressive strength adequate for the particular application, for example of greater than 0.4 MPa for some applications. The desired compressive strength is selected so that the components are in no sense free flowing, and so that the scaffold body can be handled without disintegrating into the individual body components. The desired compressive strength is also selected to provide the strength that is required to remain integral after implantation, whether for repair of a load-bearing body part or non-load-bearing part, or one subject to impact or significant movement. In some preferred embodiments, the compressive strength of the scaffold body is at least about 5 MPa, while in other embodiments where greater rigidity is required, the compressive strength is at least about 20 MPa, such as between about 20 and about 200 MPa.

The initial surface area of the scaffold varies widely depending on the scaffold morphology—for example, whether it is all fibers, the fiber dimensions, the particle size, etc. Moreover, the surface area changes during biodegradation. Generally speaking, scaffolds of the fibrous morphology have a surface area/bulk scaffold volume of between about 50 and about 1000 $cm^{-1}$, such as between about 50 and about 500 $cm^{-1}$. One exemplary scaffold has a surface area/unit bulk volume of 134 $cm^{-1}$, based on its dimensions of being a cylinder 7 mm in diameter and 2 mm high. The surface area of the starting glass fibers was 10.27 $cm^2$ and the bulk volume of the cylinder was $7.7 \times 10^{-2}$, $cm^3$.

One or more director element compounds are incorporated into the implantable material in a concentration of at least about 0.05 wt %, or at least about 0.1 wt %. In most instances, the concentration is less than 10 wt %, or less than 5 wt %, such as between about 0.05 and about 5 wt %, for example between about 0.1 and about 2.5 wt % (per compound). A director element compound is an oxide or other compound of one of the director elements Cu, Sr, Zn, Fe, Mn, Cr, V, Nb, Mo, W, Ba, Co, S, Al, Ti, Y, Mg, Si and/or Ni, for example CuO, SrO, ZnO, or $Fe_2O_3$. For example, Zn may be an oxide, carbonate, nitrate or other. While the director elements are described here and in the claims as director element compounds and described as various oxides by weight %, those skilled in the art understand that in the final glass or glass/crystalline composition, the oxide compounds are dissociated, and the specific oxides, e.g., CuO, SrO, ZnO, or $Fe_2O_3$ are not separately identifiable or even necessarily separately present. Nonetheless, it is conventional in the art to refer to the final composition as containing a given % of the individual oxides, so that is done here. So from this perspective, the oxides herein are on an equivalent basis.

Where the implantable biocompatible material is borate-based or phosphate-based, the director element concentration is less than 5 wt %, and it may be higher and up to 10 wt % where the biocompatible material is silicate-based. More than one of these director elements can be employed in a single composition. Also, certain of these elements may be present in greater amounts in that they are not being used as director elements in accordance with this invention. For example, a composition made of a biocompatible glass material which contains 0.4 wt % CuO and 15 wt % SrO contains Cu as a director element in accordance with this invention; and it contains Sr, but not as a director element in accordance with this invention. Such a material would indeed satisfy the requirement herein for a director element from the group Cu, F, Fe, Mn, Mo, Ni, Sr, and Zn in a concentration between about 0.05 and 10 wt % by virtue of the material's Cu content, regardless of its unqualifying Sr content.

Where Cu is desired as the director element, the source of Cu to the glass or crystalline biocompatible material may be a copper oxide such as CuO or $Cu_2O$ or other copper compounds such as copper nitrate or copper sulfate, for example. In one embodiment, Cu is incorporated into the glass in a CuO concentration of at least about 0.05 wt %, or at least about 0.1 wt %. In most instances, the concentration is less than 10 wt %, or less than 5 wt %, such as between about 0.05 and about 5 wt %, for example between about 0.1 and about 2.5 wt %

Where Sr is desired as the director element, the source of Sr to the glass or crystalline biocompatible material may be an oxide such as SrO or other Sr compounds such as $SrCO_3$, for example. In one embodiment, Sr is incorporated into the glass in a SrO concentration of at least about 0.05 wt %, or at least about 0.1 wt %. In most instances, the concentration is less than 10 wt %, or less than 5 wt %, such as between about 0.05 and about 5 wt %, for example between about 0.1 and about 2.5 wt %

Where Zn is desired as the director element, the source of Zn to the glass or crystalline biocompatible material may be an oxide such as ZnO or other Zn compounds such as $Zn_3(PO_4)_2$-$xH_2O$, for example. In one embodiment, Zn is incorporated into the glass in a ZnO concentration of at least about 0.05 wt %, or at least about 0.1 wt %. In most instances, the concentration is less than 10 wt %, or less than 5 wt %, such as between about 0.05 and about 5 wt %, for example between about 0.1 and about 2.5 wt %

Where Fe is desired as the director element, the source of Fe to the glass or crystalline biocompatible material may be an oxide such as FeO, $Fe_3O_4$, $Fe_2O_3$, or other Fe compounds such as $FeSO_4$-$7H_2O$, for example. In one embodiment, Fe is incorporated into the glass in a $Fe_2O_3$ concentration of at least about 0.05 wt %, or at least about 0.1 wt %. In most instances, the concentration is less than 10 wt %, or less than 5 wt %, such as between about 0.05 and about 5 wt %, for example between about 0.1 and about 2.5 wt %.

Calcium is incorporated into the compositions of the invention to facilitate the formation of calcium carbonate (such as calcite) and optionally other calcium-containing compounds upon bioreaction of the composition with bodily fluids after implantation into a mammalian host. The CaO concentration of the composition is between about 2.5 and about 50 wt %, for example between about 5 and about 40 wt %. In a preferred embodiment, the CaO concentration is between about 12 and about 25 wt %. In the composition, the oxide compounds are dissociated, and the specific CaO or other oxides are not typically not separately identifiable or even necessarily separately present. Nonetheless, it is conventional in the art to refer to the final composition as containing a given % of the individual oxides, so that is done here. This CaO concentration is typically provided in the form of a Ca compound such as CaO or $CaCO_3$, $Ca(NO_3)_2$, $Ca(OH)_2$ and others.

The director element and biocompatible composition are carefully selected and formulated to provide a specifically timed release of director element based on flow of blood or other physiological fluids through the scaffold as the biocompatible composition biodegrades in the mammalian host. The director element is an integral component of the biocompatible composition and is chemically dissolved in the material. This is in sharp contrast to being in the form of a coating on the glass or being simply adsorbed onto the material as, for example, adsorbed onto a water insoluble implantable compound. Since the director element is chemically dissolved in the glass material, it is released into the host mammal incrementally as the glass biodegrades, and over that same period during which the glass biodegrades. In contrast, a coating or adsorbed material is released more quickly, and its release cannot be controlled by controlling the composition of the overall glass material. In one embodiment, the director element is generally macro-homogeneously present in the biocompatible composition to facilitate release over the entire degradation life of the composition. As blood and or other fluids flow through the scaffold and the scaffold biodegrades in the host mammal, the director element is released to provide its advantageous angiogenic effect over time in promoting benefits to the host in the area of the implantation. So, for example, as the borate-based, phosphate-based, or silicate-based composition biodegrades, it releases director element to promote angiogenesis or some other desirable biological function.

The glass formers in certain embodiments of the invention are concentration balanced to impart the desired biodegradability. For example, in the B3-CSZ composition of below Example 1, the concentrations of the glass formers borate, silicate, and phosphate are balanced to 51.2 wt %, 0 wt %, and 3.86 wt %, respectively, and in the CSZF composition to 50.88 wt %, 0 wt %, and 3.84 wt %, respectively, with respect to themselves and with respect to the other components in the material $Na_2O$, CaO, and $K_2O$. Balancing in this regard encompasses balancing the concentration of one glass former with other components, such as with those glasses contain borate and other components, but no phosphate or silicate.

In many preferred embodiments of the scaffold, the concentrations of glass formers are balanced such that at least about 20 wt % of the biocompatible material biodegrades within six weeks of implantation in its mammalian host. For example, the concentrations of glass formers are balanced such that at least about 20 wt % of the biocompatible material biodegrades within six weeks of implantation in a Fisher 344 rat having an age between 9 and 11 weeks and a weight between 200 and 300 grams. In accord with this measure, the testing is performed on rats with a standard deviation of 25% (relative) of the biocompatible material and a population size of 10. In other words, when 10 of these scaffolds are implanted into the subcutaneous sites of rats, on average at least 20 wt % of the scaffolds' material biodegrades within six weeks; and in at least 68% of rats at least 15 wt % of the scaffold biodegrades; and in at least 90% of rats at least 10 wt % of the scaffold degrades. Biodegrading in most instances manifests itself as scaffold weight loss, but can also manifest itself as another reaction of the scaffold material involving a change of composition which results in release of director element.

Similarly, in another aspect, the concentrations of glass formers are balanced such that at least about 20 wt % of the director element concentration in the scaffold is released from the scaffold within six weeks of implantation in its mammalian host. For example, the concentrations of glass formers are balanced such that at least about 20 wt % of the director element concentration in the scaffold is released from the scaffold into the host within six weeks of implantation in a Fisher 344 rat having an age between 9 and 11 weeks and a weight between 200 and 300 grams. In accord with this measure, the testing is performed on rats with a standard deviation of 25% (relative) of the biocompatible material and a population size of 10. In other words, when 10 of these scaffolds are implanted into the subcutaneous sites of rats, on average at least 20 wt % of the scaffolds' director element concentration is released within six weeks; and in at least 68% of rats at least 15 wt % of the scaffolds' director element concentration is released; and in at least 90% of rats at least 10 wt % of the scaffolds' director element concentration is released.

On the other hand, the scaffold does not biodegrade so quickly that it does not provide its healing benefits for sufficient time. For example, at least 50 wt % of the scaffold material remains for at least two weeks and does not biodegrade within two weeks. That is, the concentrations of glass formers are balanced such that at least about 50 wt % of the biocompatible material remains for at least two weeks after implantation in a Fisher 344 rat having an age between 9 and 11 weeks and a weight between 200 and 300 grams. In accord with this measure, the testing is performed on rats with a standard deviation of 25% (relative) of the biocompatible material and a population size of 10. In other words, when 10 of these scaffolds are implanted into the rats, on average at least 50 wt % of the scaffolds' material does not biodegrade within two weeks; and in at least 68% of rats at least 37.5 wt % of the scaffold does not biodegrade within two weeks; and in at least 90% of rats at least 25 wt % of the scaffold does not biodegrade within two weeks.

Moreover, in these embodiments, at least 50 wt % of the scaffold director element concentration remains for at least two weeks. That is, the concentrations of glass formers are balanced such that at least about 50 wt % of the director element remains for at least two weeks after implantation in a Fisher 344 rat having an age between 9 and 11 weeks and a weight between 200 and 300 grams. In accord with this measure, the testing is performed on rats with a standard deviation of 25% (relative) of the biocompatible material and a population size of 10. In other words, when 10 of these scaffolds are implanted into the rats, on average at least 50 wt % of the scaffolds' director element concentration remains for at least two weeks; and in at least 68% of rats at least 37.5 wt % of the scaffolds' director element concentration remains for at least two weeks; and in at least 90% of rats at least 25 wt % of the scaffolds' director element concentration remains for at least two weeks.

As noted above, the biocompatible materials, whether in the form of scaffolds or other shapes, biodegrade in physiological fluids. However, in comparison to articles characterized as "water soluble" which dissolve relatively rapidly (over a period of, e.g., three weeks or less) in aqueous solutions, the biocompatible materials of the invention are not water soluble, that is, they are resistant to rapid water solubility. For example, scaffolds made from them having a surface area and size of practical application for use as an implantable scaffold do not completely dissolve in a less than several weeks (e.g., six weeks) at 37° C. in an aqueous phosphate solution or an aqueous solution with a miscible solvent such as methanol, ethanol, isopropanol, acetone, ethers or the like. As understood in the art, materials which are "water soluble" are subject to relatively rapid solubility; and materials which are "water insoluble" are either entirely insoluble in water, or are at least only dissolvable with difficulty. Generally speaking the scaffold materials are not water insoluble and are not water soluble under this characterization; rather, they are of intermediate water solubility.

In one embodiment the director element is incorporated into a borate-based glass material containing the following, approximately, with all percentages herein being by weight, unless stated otherwise:

| | |
|---|---|
| $B_2O_3$ | 40 to 80 |
| $Na_2O$ | 0 to 25 |
| $Li_2O$ | 0 to 25 |
| $K_2O$ | 0 to 25 |
| $Rb_2O$ | 0 to 25 |
| CaO | 2.5 to 50 (or 45) |
| MgO | 0 to 25 |
| SrO | 0 to 40 |
| BaO | 0 to 50 |
| $Li_2O + Na_2O + K_2O + Rb_2O$ | 0 to 50 cumulative |
| $MgO + SrO + BaO + CaO$ | 0 to 50 cumulative |
| $P_2O_5$ | 0 to 10 |
| $SiO_2$ | 0 to 18 |
| $Al_2O_3$ | 0 to 3 |
| F | 0 to 4 |
| transition metal elements | 0 to 10 cumulative. |

The concentrations of $K_2O$ and MgO in certain of these embodiments are each from about 1 to about 25 wt %. In most embodiments, the one or more of $Li_2O$, $Na_2O$, $K_2O$, and $Rb_2O$ is present in a cumulative concentration between about 1 and about 50 wt %, such as between about 5 and about 20 wt %; and the one or more of MgO, SrO, BaO, and CaO is present in a cumulative concentration between about 1 and about 50 wt %, such as between about 5 and about 40 wt %. Where Cu is the director element, this composition further contains at least about 0.05 wt %, or at least about 0.1 wt %, such as between about 0.05 and about 5 wt %, for example between about 0.1 and about 2.5 wt % CuO. The transition metal elements are those elements where the d-band contains less than its maximum number of ten electrons per atom, and includes, among others, Co and Ni. In fact, certain of the director elements used in accordance with this invention such as Zn and Fe are transition metals. So in formulations where the director element concentration of these director elements is stated to be in a particular range such as between about 0.1 and about 2.5 wt %, of course the director element concentration is in that range regardless of the fact that transition elements may be among the director elements, and if Zn and Fe are present in an amount greater than 2.5 wt %, they are not director elements.

In most embodiments the biocompatible material consists only or essentially of components meeting these compositional requirements or other narrower descriptions herein. But generally speaking, for some embodiments other materials not meeting these descriptions may be incorporated into the scaffolds.

It can therefore be appreciated that in addition to the director element, the borate-based biocompatible materials in certain embodiments include 40 to 80 wt % $B_2O_3$ or 50 to 80 wt % $B_2O_3$, or even the narrower $B_2O_3$ ranges described herein, in combination with 1 to 25 wt % $Na_2O$, 1 to 25% $K_2O$, 1 to 40 wt % CaO, 1 to 25 wt % MgO, and 1 to 10 wt % $P_2O_5$. Or the component materials may contain 40 to 80 wt % $B_2O_3$, 1 to 25 wt % $Li_2O$, and 5 to 40 wt % CaO. Or they may contain 40 to 80 wt % $B_2O_3$, 1 to 25 wt % $Na_2O$, and 1 to 40 wt % CaO. Or they may contain 40 to 80 wt % $B_2O_3$, 1 to 25 wt % $Na_2O$, and 1 to 40 wt % BaO. Or they may contain 40 to 80 wt % $B_2O_3$, 1 to 25 wt % $Li_2O$, and 1 to 25 wt % MgO. Or they may contain 40 to 80 wt % $B_2O_3$, 1 to 25 wt % $Li_2O$, and 1 to 40 wt % BaO.

While the biocompatible materials hereinabove and hereinbelow are described as containing various oxides by weight %, those skilled in the art understand that in the final glass or glass/crystalline composition, the oxide compounds are dissociated, and the specific oxides, e.g., $B_2O_3$, $SiO_2$, $P_2O_5$, etc. are not separately identifiable or even necessarily separately present. Nonetheless, it is conventional in the art to refer to the final composition as containing a given % of the individual oxides, so that is done here. So from this perspective, the compositions herein are on an equivalent basis.

The biocompatible materials of the invention containing the director element in certain preferred versions are borate-based in that they contain between about 40 and about 80 wt % $B_2O_3$, such as between about 50 and about 80 wt % $B_2O_3$. Borate-based materials have several important advantages for biological use such as their ease of preparation, ability to be made into glass particulates, microspheres or fibers at relatively low temperatures without crystallization, their angiogenicity and bacteriostaticity, and, particularly, their biocompatibility. The borate-based materials disclosed herein, compared to silicate-based materials, have significantly faster—e.g., 3 to 10 times—reaction rates, lower melting temperatures, resistance to crystallization, and in certain instances the absence of silica, which only slowly degrades in the body. So while certain embodiments employ up to about 18 wt % $SiO_2$ in many other preferred embodiments herein, the materials are silica-free, containing less than 0.1 wt % silica or even no silica. Upon reaction in vitro, interior segments of the borate-based fibers become excavated and in fact hollow as interior borate material biodegrades. Upon reaction in vivo, interior segments of borate-based fibers become excavated as interior borate material biodegrades and is filled with soft tissue, including blood vessels, bodily fluids, and the like. Accordingly, in vivo the fibers after bioreaction have tubular and hollow aspects which are filled with soft tissue, as the initially hollow interior of the fiber is replaced with soft tissue including blood vessels, bodily fluids, and the like. The borate materials described herein also release boron in vivo as they react with the bodily fluids.

In one preferred embodiment, the material contains between about 50 and about 80 wt % $B_2O_3$; between about 5 and about 20 wt % alkali oxide component selected from the group consisting of $Li_2O$, $Na_2O$, $K_2O$, $Rb_2O$, and combinations thereof; and between about 5 and about 40% alkaline earth component selected from the group consisting of MgO, SrO, BaO, and combinations thereof. Lanthanides are specifically and strictly excluded from certain preferred embodiments. In some embodiments the biocompatible material consists essentially of between about 50 and about 80 wt % $B_2O_3$; between about 5 and about 20 wt % alkali oxide component selected from the group consisting of $Li_2O$, $Na_2O$, $K_2O$, $Rb_2O$, and combinations thereof; between about 5 and about 40 wt % alkaline earth component selected from the group consisting of MgO, SrO, BaO, and combinations thereof, and between about 0.05 and 5 wt % director element.

In certain embodiments of the invention, the biocompatible material is selected to include at least two of the alkali oxides $Li_2O$, $Na_2O$, $K_2O$, and/or $Rb_2O$ in a cumulative concentration of between about 5 and about 25 wt %, such as between about 8 and 20 wt %. It has been discovered to be advantageous to include two or more such alkali compounds in order to reduce the tendency for crystallization, which ultimately improves the workability and manufacturability of the glasses, which can be important to making scaffolds. Using more than one type of alkali (i.e., mixed alkali) can reduce the cost of a glass, modify its reaction rate with bodily fluids, and provide additional elements beneficial to tissue growth and regeneration.

A further feature of certain embodiments is that the cumulative concentration of the alkaline earth oxides from the group consisting of MgO, SrO, BaO, CaO, and combinations thereof is in the range of 1 to about 50 wt %, such as in the range of 1 to 30 wt %, or even about 8 to 25 wt %. Certain of these embodiments contain two or more such alkaline earth oxides in a range of 1 to 45 wt % cumulatively, such as in the range of 5 to 25 wt %. If SrO is present in a concentration which yields a Sr concentration above 10 wt %, it does not qualify as a director element in accordance with this invention.

These embodiments into which the director element may be incorporated and which employ mixed alkali oxide contents contain $B_2O_3$ from about 40 to about 80 wt %. Certain of these embodiments consist essentially of $B_2O_3$ from about 40 to about 80 wt %, mixed alkali oxides selected from the group consisting of $Li_2O$, $Na_2O$, $K_2O$, and $Rb_2O$, and one of MgO, SrO, BaO, or CaO, plus the Cu containing compound. Other embodiments consist essentially of $B_2O_3$ from about 40 to about 80 wt %, two or more alkali oxides selected from the group consisting of $Li_2O$, $Na_2O$, $K_2O$, and $Rb_2O$, and two or more alkaline earth oxides from the group consisting of MgO, SrO, BaO, and CaO, plus the Cu containing compound. For example, the first four compositions in the table in Example 1 consist essentially of $B_2O_3$ from about 40 to about 80 wt %, two or more mixed alkali oxides selected from the group consisting of $Li_2O$, $Na_2O$, $K_2O$, and $Rb_2O$ in a cumulative wt % between 5 and 25%, and two or more from among MgO, SrO, BaO, and CaO in a cumulative wt % between 8 and 25%. Other embodiments optionally include one or more of $P_2O_5$, $SiO_2$, $Al_2O_3$, F, and transition metal elements.

The invention includes incorporating director element into biocompatible materials with an especially high $B_2O_3$ composition, namely, from about 60 to about 82 wt %, still more preferably from about 70 to about 80 wt %. These embodiments employ an alkali oxide selected from the group consisting of $Li_2O$, $Na_2O$, $K_2O$, $Rb_2O$, and combinations thereof cumulatively from about 1 to about 50 wt %, such as from about 5 to about 25 wt %, and even from about 8 to about 20 wt %; and even optionally two or more such oxides cumulatively in this range. They also employ alkaline earth oxides from group consisting of MgO, SrO, BaO, CaO, and combinations thereof in the range of about 1 to about 50 wt %, such as in the range of 1 to 30 wt %, or even about 8 to 25 wt %, and even two or more such oxides cumulatively in this range The invention also encompasses a biocompatible composition for implantation into a mammal to facilitate vessel growth in repair, regeneration, and/or proliferation of bodily tissue, wherein the biocompatible material is phosphate-based or silicate-based and is at least partially dissolvable in mammalian bodily fluids, and the director element is incorporated into the biocompatible material in a concentration as described above. In these embodiments, $P_2O_5$ and/or $SiO_2$ are glass formers and constitute about 20 to about 65 wt % $P_2O_5$ or about 20 to about 60 wt % $SiO_2$. These materials also contain an alkali metal oxide component of, for example, one or more of $Li_2O$, $Na_2O$, $K_2O$, $Rb_2O$, $Cs_2O$, or a mixture thereof in a concentration of about 8 wt % to about 55 wt %, such as about 10 to about 52 wt %. These phosphate- and silicate-based glasses also contain a calcium component, one of CaO, $CaF_2$, or mixtures thereof. For example, many of these glasses contain from about 5 to about 40 wt % of CaO or $CaF_2$, or mixtures thereof, such as about 10 to about 30 wt % of CaO or $CaF_2$, or mixtures thereof, or about 10 to about 15 wt % of CaO or $CaF_2$, or mixtures thereof. Accordingly, one of these embodiments contains about 20 to about 65 wt % $P_2O_5$, and one or more of $Li_2O$, $Na_2O$, $K_2O$, $Rb_2O$, $Cs_2O$, or a mixture thereof in a concentration of about 8 wt % to about 55 wt %, and a calcium component of in a concentration of about 5 to about 40 wt % of CaO or $CaF_2$, and Cu in a concentration of about 0.05 to about 5 wt %, such as between about 0.1 and about 2.5 wt %. Another embodiment contains about 20 to about 65 wt % $P_2O_5$, and one or more of $Li_2O$, $Na_2O$, $K_2O$, $Rb_2O$, $Cs_2O$, or a mixture thereof in a concentration of about 10 wt % to about 52 wt %, a calcium component of CaO or $CaF_2$ or mixtures thereof in a concentration of about 5 wt % to about 40 wt % of CaO or $CaF_2$ or mixtures thereof, and Cu in a concentration of about 0.05 to about 5 wt %, such as between about 0.1 and about 2.5 wt %. Another embodiment contains about 20 to about 65 wt % $P_2O_5$, and one or more of $Li_2O$, $Na_2O$, $K_2O$, $Rb_2O$, $Cs_2O$, or a mixture thereof in a concentration of about 8 wt % to about 55 wt %, a calcium component of CaO or $CaF_2$ or mixtures thereof in a concentration of about 10 to about 30 wt % of CaO or $CaF_2$ or mixtures thereof, and Cu in a concentration of about 0.05 to about 5 wt %, such as between about 0.1 and about 2.5 wt %. Another of these embodiments contains about 20 to about 60 wt % $SiO_2$, and one or more of $Li_2O$, $Na_2O$, $K_2O$, $Rb_2O$, $Cs_2O$, or a mixture thereof in a concentration of about 8 wt % to about 55 wt %, a calcium component of CaO in a concentration of about 5 to about 40 wt % of CaO or $CaF_2$, and Cu in a concentration of about 0.05 to about 5 wt %, such as between about 0.1 and about 2.5 wt %. Another embodiment contains about 20 to about 60 wt % $SiO_2$, and one or more of $Li_2O$, $Na_2O$, $K_2O$, $Rb_2O$, $Cs_2O$, or a mixture thereof in a concentration of about 10 wt % to about 52 wt %, a calcium component of CaO or $CaF_2$ or mixtures thereof in a concentration of about 5 wt % to about 40 wt % of CaO or $CaF_2$ or mixtures thereof, and Cu in a concentration of about 0.05 to about 5 wt %, such as between about 0.1 and about 2.5 wt %. Another embodiment contains about 20 to about 60 wt % $SiO_2$, and one or more of $Li_2O$, $Na_2O$, $K_2O$, $Rb_2O$, $Cs_2O$, or a mixture thereof in a concentration of about 8 wt % to about 55 wt %, a calcium component of CaO or $CaF_2$ or mixtures thereof in a concentration of about 10 to about 30 wt % of CaO or $CaF_2$ or mixtures thereof, and Cu in a concentration of about 0.05 to about 5 wt %, such as between about 0.1 and about 2.5 wt %. In certain of these embodiments, $CaF_2$ is strictly avoided and the calcium component is CaO.

Examples of silicate-based biocompatible material containing director elements in accordance with this invention are as follows:

| Glass | $SiO_2$ | $Na_2O$ | $P_2O_5$ | CaO | CuO | FeO | $CaF_2$ | $B_2O_3$ | ZnO | MnO | MgO | $K_2O$ |
|---|---|---|---|---|---|---|---|---|---|---|---|---|
| A | 44.6 | 24.3 | 5.9 | 24.3 | 1.0 | | | | | | | |
| B | 44.1 | 24.0 | 5.9 | 24.0 | 2.0 | | | | | | | |
| C | 43.7 | 23.8 | 5.8 | 23.8 | 3.0 | | | | | | | |
| D | 43.2 | 23.5 | 5.8 | 23.5 | 4.0 | | | | | | | |
| E | 42.8 | 23.3 | 5.7 | 23.3 | 5.0 | | | | | | | |
| F | 44.0 | 25.0 | 6.0 | 20.0 | 0.2 | 0.2 | 1.0 | 2.2 | 0.6 | 0.2 | 0.6 | |
| G | 50.0 | 6.0 | | 19.0 | 0.2 | 0.2 | 1.0 | 3.0 | 1.0 | 0.2 | | 12.0 |

Examples of phosphate-based biocompatible glass containing director elements in accordance with this invention are as follows:

| Glass ID | $Na_2O$ | $K_2O$ | CaO | MgO | $B_2O_3$ | $P_2O_5$ | $Li_2O$ | SrO | CuO |
|---|---|---|---|---|---|---|---|---|---|
| P-1 | 3.8 | 5.8 | 27.5 | 2.5 | 0.0 | 60.0 | 0.0 | 0.0 | 0.4 |
| P-2 | 9.2 | 9.3 | 27.5 | 0.0 | 0.0 | 53.5 | 0.0 | 0.0 | 0.5 |
| P-3 | 7.8 | 11.8 | 17.0 | 7.6 | 0.0 | 55.2 | 0.0 | 0.0 | 0.6 |
| P-4 | 7.8 | 11.8 | 17.0 | 7.6 | 0.0 | 55.2 | 0.0 | 0.0 | 0.6 |
| P-5 | 6.6 | 8.9 | 21.9 | 0.0 | 4.1 | 58.0 | 0.0 | 0.0 | 0.5 |
| P-6 | 10.5 | 0.0 | 23.0 | 0.0 | 4.0 | 61.1 | 1.1 | 0.0 | 0.3 |
| P-7 | 8.0 | 3.7 | 1.5 | 0.0 | 1.8 | 78.1 | 0.0 | 6.7 | 0.2 |

These phosphate-based formulations demonstrate situations where it is advantageous to include at least two of the alkali oxides $Li_2O$, $Na_2O$, $K_2O$, and/or $Rb_2O$ in a cumulative concentration of between about 5 and about 25 wt %, such as between about 8 and 20 wt %. As noted above, it has been discovered to be advantageous to include two or more such alkali compounds in order to reduce the tendency for crystallization, which ultimately improves the workability and manufacturability of the glasses, which can be important to making scaffolds. Using more than one type of alkali (i.e., mixed alkali) can reduce the cost of a glass, modify its reaction rate with bodily fluids, and provide additional elements beneficial to tissue growth and regeneration. In one embodiment Na and K are incorporated into the glass and upon dissolution the glass releases both of these necessary elements to the host's bodily fluids.

A further feature of these phosphate-based embodiments is that the cumulative concentration of the alkaline earth oxides from the group consisting of MgO, SrO, BaO, CaO, and combinations thereof is in the range of 1 to about 50 wt %, such as in the range of 1 to 30 wt %, or even about 8 to 25 wt %. Certain of these embodiments contain two or more such alkaline earth oxides in a range of 1 to 45 wt % cumulatively, such as in the range of 5 to 25 wt %.

The biocompatible materials of the invention are in the form of solid fibers, hollow fibers, ribbons, solid spheres, hollow spheres, particles, and combinations thereof. In an especially preferred embodiment for many applications, the composition is in the form of a scaffold body which includes fibers, and in certain such embodiments it is a scaffold body which consists essentially of components which are fibers. The fibers have an aspect ratio of at least 2:1 length:transverse dimension (e.g., diameter), and more typically at least 5:1, such as greater than 10:1. In certain embodiments of the invention, the scaffold body components are primarily one form, such as fibers, in combination with a minor constituent of a second form from the foregoing options, such as microspheres.

There is also an option with this invention of employing distinct component compositions to strategically impart certain properties. For example, the composition in some embodiments is "blended" in that it employs 10 to 90 wt % of components having one composition selected from the above, and 10 to 90 wt % of components of a different composition. Or even more than two such types of components may be employed. That is, the material may contain at least 10 wt % of components comprising a first component material within the contemplated compositions and at least 10 wt % of components comprising a second component material, wherein the first and second component materials have compositions measurably distinct from each other. And it is contemplated that only the first component material may contain the director element, or that the director element may be present in both materials in different amounts. This permits the selection of, for example, faster reacting fibers in combination with slower reacting fibers; or the selection of Ca-containing fibers with Ca-free fibers. One can therefore select standard composition components and combine them with non-standard composition components to effectively customize or dope the scaffold for the application presented, or for the host's particular needs. Alternatively, hollow spheres containing a growth factor or drug for delivery to the host can be incorporated with other structural components, such as fibers.

In one embodiment the director element is incorporated into the materials and a scaffold is formed to have a porosity which is selected to provide fluid flow into the scaffold to facilitate uptake of bodily fluids, while maintaining sufficient strength for handling and implantation. The porosity is between about 15 vol % and about 90 vol %. There are different levels of porosity, for example between about 15 and about 30 vol %, or between about 30 and about 60 vol %, or between about 60 and about 90%, which are preferred for different applications. Porosity depends on or is controlled by many factors such as fiber orientation, shape of particles or microspheres, and the thermal treatment (time/temperature) used to bond the elements together. Independent of this bulk porosity, interconnectivity is also important in embodiments of the invention which are in the form of scaffolds. Because tissue repair is strongly influenced by the flow of bodily fluids into the scaffold, it is preferred to have a high level of interconnectivity of pores within the scaffold, and a low level of closed pores. That is, it is important that most pores be connected to other pores, and that there is a direct or indirect path from most pores to the exterior surface of the scaffold. In certain embodiments, at least about 80 vol %, such as at least about 90%, of the pore volume of the scaffold is directly or indirectly through other pores accessible from the scaffold exterior, and therefore accessible to bodily fluids. The scaffold has interconnectivity of at least about 75%, preferably at least about 85%, by which it is meant that at least 75% or 85% by volume of the pores is interconnected.

The method of making the biocompatible materials is not narrowly critical to the invention. By way of example, in preparing the biocompatible materials, individual analytical reagent grade components are weighed, mixed thoroughly, and melted in a platinum crucible at temperatures between 1000 to about 1500° C., depending upon composition for approximately one to four hrs. The melt is then quenched, for example, on a steel or copper plate to form glass that can be ground into particulates of a desired size. The particulates can be spheroidized to form microspheres of a chosen diameter. The material of certain preferred compositions when in the form of a melt can easily be formed into fibers. If fibers of the borate glass are made, they can either be pulled by hand directly from the melt or pulled through bushing by a rotating drum.

The components can be self-bonded to form three dimensional scaffolds by simply heating an assemblage of particulates in a furnace and allowing the fibers/particles/spheres to soften and bond to each other. After the allotted time at temperature, the construct is removed from the furnace and cooled to room temperature. Many prior biocompatible glasses, such as 45S5, are difficult to self bond due to crystallization of the glass. Therefore the self-bonding ability of borate glasses is a distinct advantage over other biocompatible materials currently in use.

In one embodiment the invention is a scaffold adapted for soft tissue growth which is prepared from fibers which are aligned so that a majority of the fibers are substantially aligned in a parallel direction. The scaffold is prepared by placing and orienting fibers in a unidirectional manner in a mold. The fibers in the mold are heated to a temperature where the fibers soften and bond together. In one preferred embodiment, the fibers are self bonded in the sense that no adhesive or other external bonding agent is used for bonding. An alternative embodiment employs a biocompatible agent or adhesive to facilitate bonding, such that the fibers are not self bonded, at least in part. Upon cooling, the assemblage of bonded fibers is sufficiently rigid and strong that the assemblage can be removed from the mold and handled. The scaffold is sufficiently rigid that it can be implanted into a mammal where it facilitates the repair and regeneration of hard tissue such as bone (including cortical and cancellous) or soft tissue such as muscle, cartilage, skin, organ, or other hard or soft tissue.

The orientation of the fibers in a lengthwise direction in the self-bonded scaffold provides lengthwise channels (or connected pores) among the fibers, which channels provide for uptake into the scaffold of stem cells, growth factors, medicines, proteins, red blood cells and other physiological materials and components carried in bodily fluids. The fibers are arranged to define channels within the scaffold which facilitate fluid flow into and lengthwise within the scaffold from one end to the other end. The orientation also provides for channels in a transverse direction generally perpendicular to the lengthwise direction of the oriented fibers, to facilitate uptake of fluids from the outer surface of the interior or core of the scaffold. These longitudinal and transverse channels exert significant capillary forces on a liquid which cause the liquid to be drawn into the scaffold. This capillary action facilitates the distribution of these fluids and components relatively uniformly throughout the scaffold and enables fluids to flow from one end of the scaffold to the other or to enter the scaffold from its surface and draw the liquid inward to the center and ends of the scaffold.

The invention in one embodiment employs fibers having a diameter, prior to molding and softening, between about 20 and about 5000 microns, such as between about 50 and about 5000 microns. In one embodiment the scaffold is prepared from fibers having diameters between about 100 and about 450 microns, such as between about 100 and about 300 microns. In an alternative embodiment, the scaffold is prepared from fibers having diameters up to about 3000 or 5000 microns (3 to 5 mm), which can be deemed more akin to rods than fibers in some contexts, but for purposes of the discussion of this invention fall within the definition of "fibers."

In one aspect of the invention employing co-aligned fibers, at least about 75 or 85% by volume of the fibers in the scaffold are longitudinally co-aligned. In this regard the fibers are co-aligned longitudinally, where "co-aligned longitudinally" and the like phrases (e.g., "in lengthwise co-alignment") as applied to a group of adjacent, bundled, or joined fibers in this application means that the alignment of each fiber in the group at any one place along at least about 75% of its length does not deviate more than about 25 degrees from parallel to the central axis of the scaffold. For illustration, an example of co-alignment is the alignment of individual wires or filaments in a multistrand/filament cable. In one preferred embodiment, each fiber in the group at any one place along at least about 75% of its length does not deviate more than about 15 degrees from parallel to the central axis of the scaffold. In another preferred embodiment, each fiber in the group at any one place along at least about 75% of its length does not deviate more than about 10 degrees from the central axis of the scaffold. So it is evident that this co-alignment aspect does not require 100% precise co-alignment of all fibers. The longitudinal co-alignment aspect also allows for some minor deviation of specific segments of individual fibers to an orientation outside these 25, 15, and 10 degree requirements. This is reflected in the requirement that the longitudinal co-alignment is of each fiber along at least 75% of its length, rather than necessarily along its entire length. So up to about 25% of the length of an individual fiber may be misaligned because, for example, it was bent during the scaffold-making process or otherwise. Each fiber in the scaffold is not absolutely straight, nor is it lying along an absolutely straight line strictly parallel to all other fibers in the scaffold. And each fiber is oriented generally in the same direction, but each is not oriented in exactly the same direction. Moreover, the scaffold itself in certain embodiments is curved, bent, or otherwise not straight, in which cases the central axis of the scaffold to which the alignment of the fibers is within 25 degrees of parallel is also curved, bent, or otherwise not straight. In the case of a curved scaffold, the fibers must be small enough in diameter to be sufficiently flexible to take on a curved configuration without breaking. In certain embodiments a straight or curved scaffold is machined into a more complex shape, in which instance the scaffold central axis refers to the central axis as molded and prior to machining.

In order to allow capillary action and channel-forming, the scaffold theoretically contains at least three fibers, although the scaffold typically comprises dozens and even hundreds of fibers. The fibers lie generally lengthwise of the scaffold central axis A (i.e., lie generally in the direction of the central axis) and are generally free of helical orientation about the scaffold central axis. This arrangement applies to at least about 75 vol % of the fibers and preferably to substantially all of the fibers.

The aspect of this embodiment that the fibers are co-aligned longitudinally contemplates that the fibers are positioned so that they have a similar alignment, which similar alignment may be straight, bent, or curved. In most embodiments they are non-helical. In a separate and distinct aspect of certain preferred embodiments, this common alignment is limited to a generally straight alignment along at least about 75%, 85%, or 95% of the length of the fibers. In other words, at least about 75%, 85%, or 95% of each fiber is generally straight, i.e., at least about 75%, 85%, or 95% of the length of each fiber has an alignment which is within 10 degrees of a mean straight central axis for the fiber. So up to 5%, 15%, or 25% of the length of each fiber may be curved, bent, or otherwise deviate more than 10 degrees from straight in relation to the overall fiber length, but the rest of each fiber is generally straight in that it so deviates less than 10 degrees. In one preferred embodiment, substantially the entire length of each fiber is generally straight in that it deviates less than 10 degrees from the fiber's average central axis. The "mean straight central axis" is the imaginary central axis for the fiber which is absolutely straight and is an average of all axes along the fiber length.

The fibers in the scaffold of these embodiments are selected to have characteristics suitable for the specific application. In one embodiment, the fibers have a length between about 2 mm and about 150 mm, such as between about 2 and about 20 mm, between about 12 mm and about 100 mm, or between about 25 mm and about 75 mm. Each fiber has a length which is at least about 10 times its diameter. "Diameter" as used herein refers to the fiber's largest dimension transverse to its length, and it does not imply that the fibers are perfectly circular in cross section. Each fiber therefore has a fiber lengthwise dimension which is at least about 10 times the fiber transverse dimension, e.g., diameter. In one embodiment, the fiber length is selected so that all, substantially all, or at least about 85 vol % of the individual fibers extend the entire length of the scaffold. The fibers may be selected to have a pre-molding, pre-joining length which corresponds to the length of the scaffold. Or in most embodiments, the length of the fibers is longer than the desired ultimate scaffold length, and the scaffold is cut to the desired length after molding and joining. In an alternative embodiment, the length of a substantial portion (e.g., at least 40 vol %) or all of the fibers is significantly less than the entire length of the scaffold.

The scaffold in these embodiments is manufactured to have a sufficiently high open and interconnected porosity from end to end of the scaffold to facilitate capillary flow of fluids such as bodily fluids and medicines and components they carry through the length of the scaffold, as well as generally transverse from outside walls of the scaffold into the scaffold interior in directions generally transverse to the longitudinal dimension of the fibers. And the scaffold is manufactured so that the ultimate porosity is low enough that the scaffold has the required strength for handling, implantation, and service after implantation. If the porosity is too high, the scaffold risks breakage in service, depending on where it is implanted and the loads it encounters. In a preferred embodiment, the porosity as measured in volume is between about 10% and about 35%, for example between about 10% and about 30%, or between about 10% and about 25%. The porosity is controllable mainly by controlling the degree of softening of the fibers during thermal treatment, in that highly softened fibers fuse together more completely to a structure with lower porosity. The degree of softening and fusing is controlled by controlling the bonding temperature and time. Porosity is also affected by the fiber diameter and by the range in fiber diameter within a given scaffold. Porosity tends to increase with an increasing range in fiber diameter.

The biocompatible material may be glassy, glass ceramic, or ceramic in nature. However the glassy state is preferred in this invention because, generally speaking, glassy materials are easier to form into different shapes, bond at lower temperatures and are more chemically homogeneous than their crystalline or partially crystalline counterparts of the same composition. It is therefore preferable that the biocompatible material is substantially glass in that less than about 5 wt %, more preferable less than 1 wt %, of the component material is crystalline material. More particularly, it is preferable that there is less than 5 wt %, preferably less than 1 wt %, crystallization when the material is heated to a temperature needed to bond the individual glass particles together. By way of example, in one embodiment it is preferable that there is less than 5 wt %, preferably less than 1 wt %, crystallization when the material is heated to 800° C. at an average heating rate of 20° C./min, held at that temperature for 10 minutes, then cooled to room temperature by exposure to STP conditions of room temperature and atmospheric pressure. More preferably, the glass will contain less than 5 wt % crystallization, even more preferably less than 1 wt % crystallization, after being heated to 575° C. with a ramp rate of 20° C./min, and held at that temperature for 20 minutes, then cooled to room temperature by exposure to STP conditions. The fibers used in many embodiments of the invention, consistent with the foregoing description, are at least 99 wt % an amorphous or non-crystalline solid, for example made by fusing a mixture of oxides such as one or more of $SiO_2$, $B_2O_3$, $P_2O_5$ (known as glass forming oxides) with basic oxides such as the alkali and alkaline earth oxides, along with the director element. In an alternative embodiment, the fibers include glass ceramics fibers that contain both glassy and crystalline regions which in many respects function in the same manner as a fiber that is completely (100%) non-crystalline. It is acceptable in some applications if the glass fiber crystallizes during the bonding step. Some of the fibers may alternatively be pre-reacted prior to bonding for the purpose of forming a thin surface layer of different chemical composition, for example, a deakalized layer, or a thin layer of hydroxyapatite or other biologically useful substance (tricalcium phosphate, octacalcium phosphate, dihydrogen calcium phosphate).

Example 1

Several glasses were prepared with the following compositions:

| Glass | $B_2O_3$ | $SiO_2$ | $Na_2O$ | CaO | $K_2O$ | MgO | $P_2O_5$ | CuO | SrO | ZnO | $Fe_2O_3$ |
|---|---|---|---|---|---|---|---|---|---|---|---|
| 13-93B3 | 53.00 | | 6.00 | 20.00 | 12.00 | 5.00 | 4.00 | | | | |
| B3 Cu-3 | 52.79 | | 5.98 | 19.92 | 11.95 | 4.98 | 3.98 | 0.40 | | | |
| B3-CS | 51.73 | | 5.86 | 19.52 | 11.71 | 4.88 | 3.90 | 0.40 | 2.00 | | |
| B3-CSZ | 51.20 | | 5.80 | 19.32 | 11.59 | 4.83 | 3.86 | 0.40 | 2.00 | 1.00 | |
| B3-CSZF | 50.88 | | 5.76 | 19.20 | 11.52 | 4.80 | 3.84 | 0.40 | 2.00 | 1.00 | 0.40 |
| 93-CSZF | | 50.88 | 5.76 | 19.20 | 11.52 | 4.80 | 3.84 | 0.40 | 2.00 | 1.00 | 0.40 |

Figure 1B:
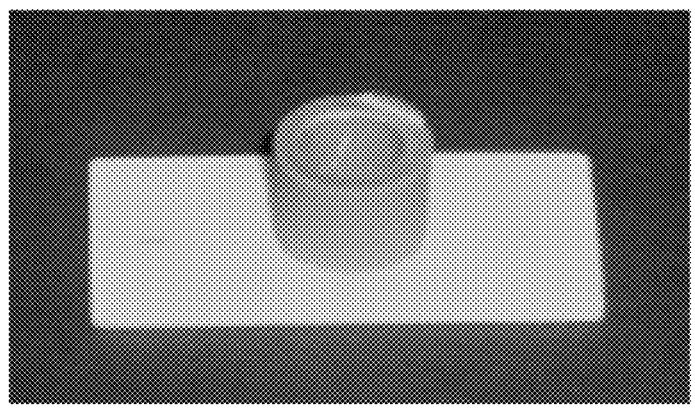
FIG. 1B shows a ceramic mold used to hold the fibers during the heat treatment.
Figure 1C:
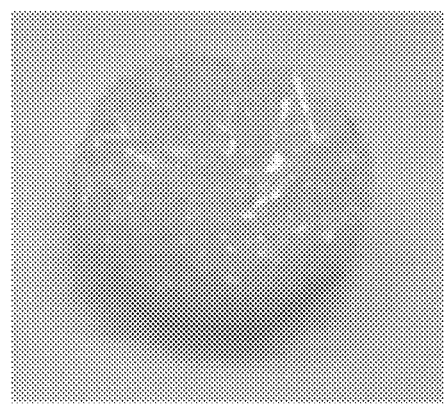
FIG. 1C is an example of a scaffold that weighs 70 mg and has dimensions of 7 mm in diameter and 2 mm thick. Scaffold porosity is 50±2%.

Scaffolds were prepared from glasses B3 Cu-3, B3 CS, B3 CSZ, and B3 CSZF. Continuous fibers of these glasses were broken into lengths of two to three millimeters (FIG. 1A), placed in a ceramic mold in a random fashion, and heated to 575° C. for 45 minutes to bond the fibers into rigid scaffolds as shown in FIG. 1B. After heating, the molds were removed from the furnace, and cooled to room temperature. Once at room temperature, the scaffolds were removed from the molds and ready for use. An example of a scaffold is shown in FIG. 1C. The scaffolds were 2 mm thick and 7 mm in diameter, and weighed ~70 mg.

Example 2

Figure 2:
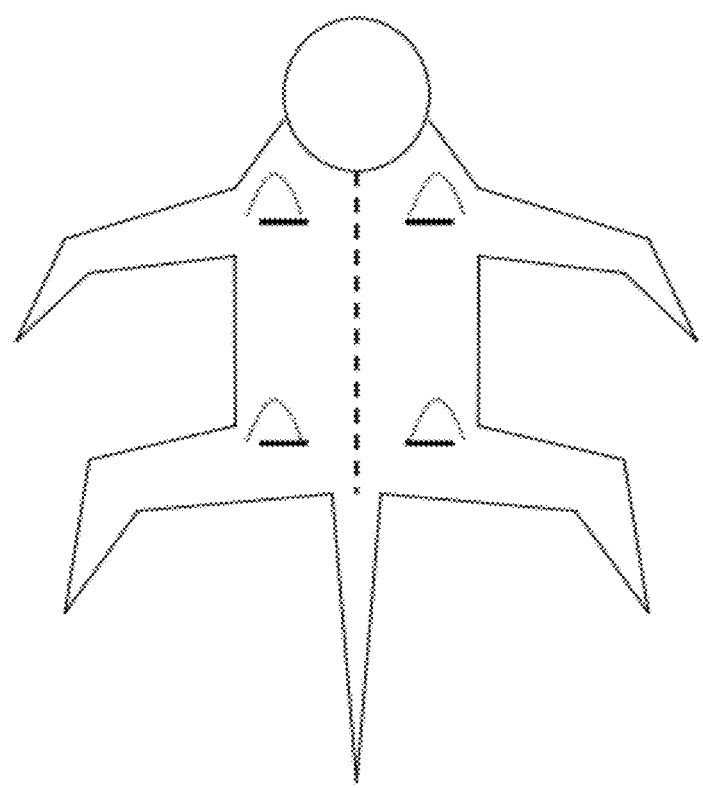
FIG. 2 is a schematic showing subcutaneous scaffold implant sites located on the back of a rat.
Figure 3:
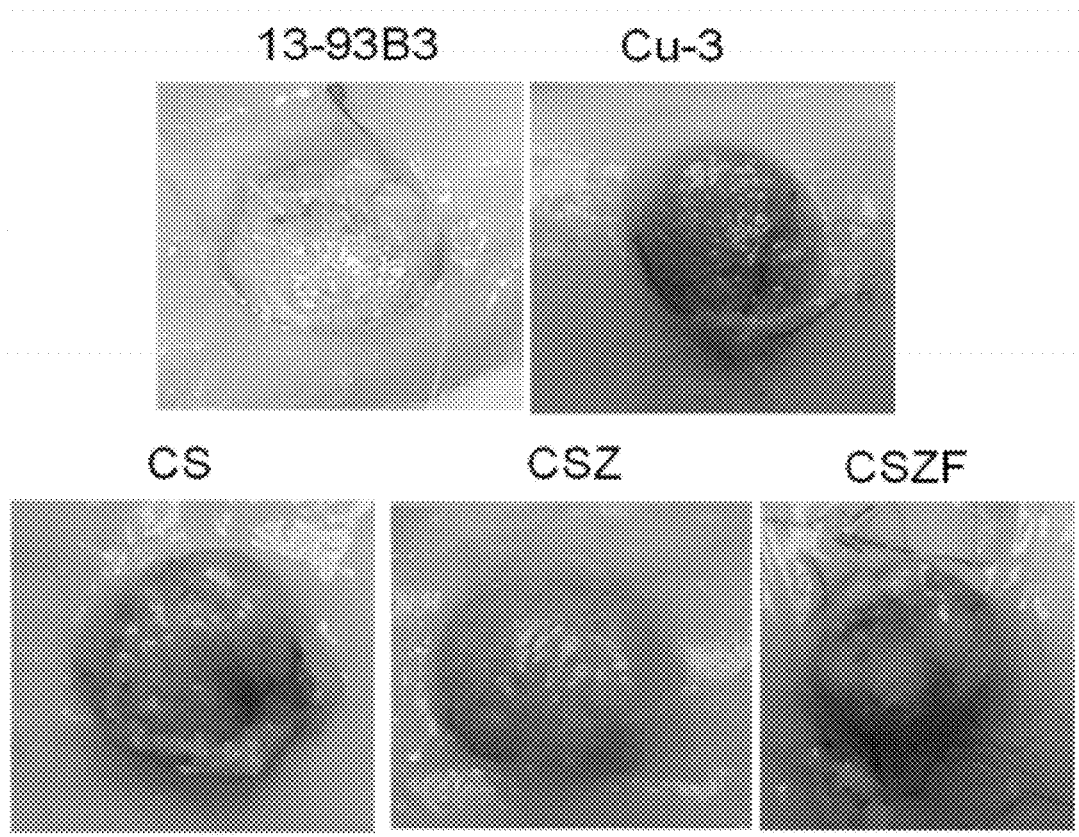
FIG. 3 shows glass scaffolds according to the invention after six weeks implantation, except for the 13-93B3 scaffold which was implanted for four weeks.

Five scaffolds of each glass were seeded with mesenchymal stem cells, and five were unseeded. The scaffolds were implanted into one of four possible locations in the subcutaneous tissue of Fisher 344 rats having an age between 9 and 11 weeks and a weight between 200 and 300 grams as shown in FIG. 2 for six weeks. A scaffold was placed above each of the front shoulders and above both hind legs as indicated. The cut made in the skin shown by the horizontal lines was approximately 20 mm wide and the pocket made under the skin (dotted line) is about 20 mm long. The dashed line represents the spine as a reference. Representative images of the appearance of each scaffold upon extraction are shown in FIG. 3. Soft tissue had infiltrated into each scaffold and significant vascular growth had occurred.

Example 3

Figure 4:
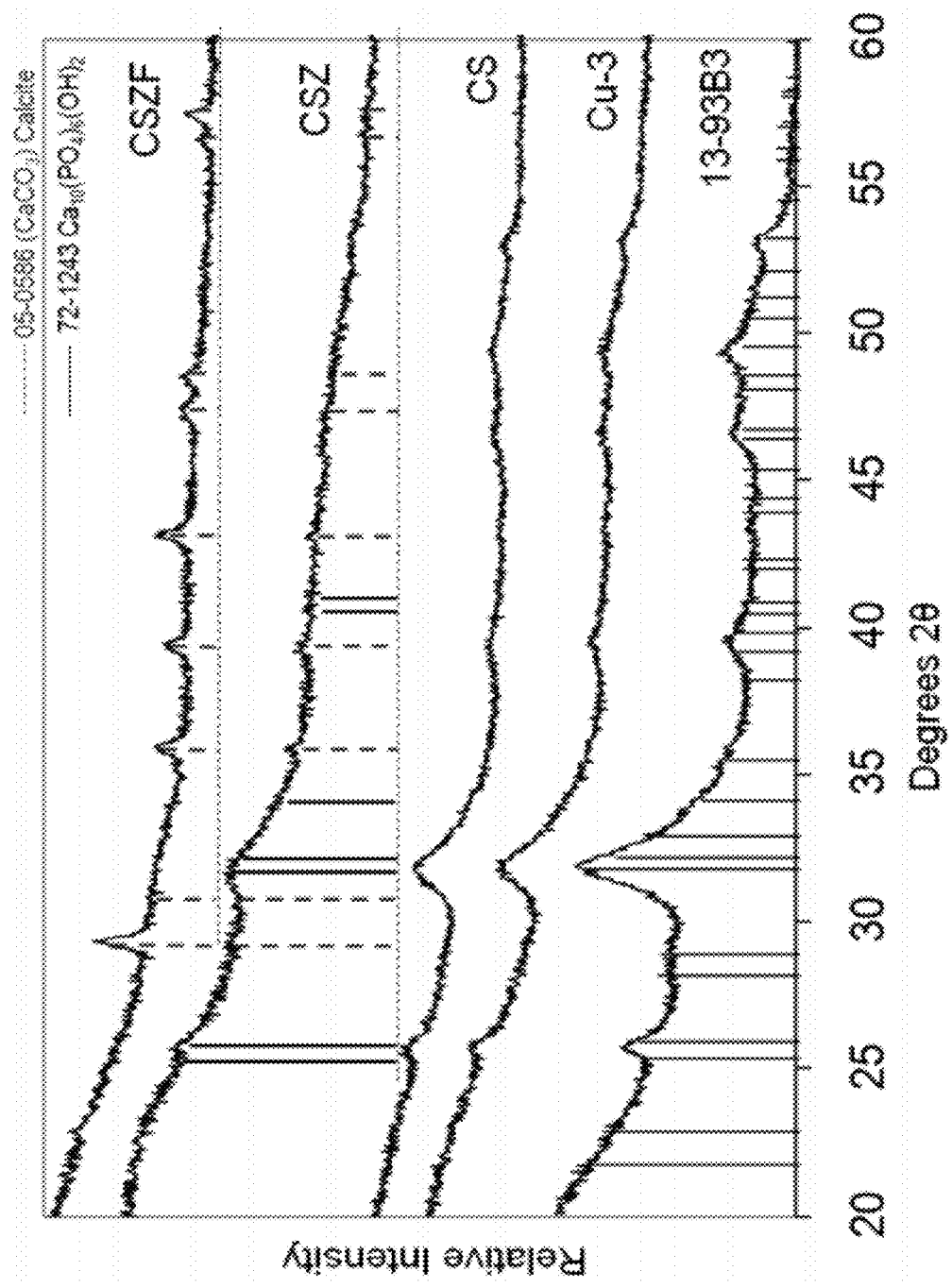
FIG. 4 shows XRD patterns for randomly oriented scaffolds according to the invention after implantation. The respective lines have been displaced vertically for clarity.

A scaffold of each type was x-rayed after removal from the rats to identify any crystalline phases formed while in the animal. The XRD patterns for each scaffold are shown in FIG. 4. The B3 Cu-3 and B3 CS glasses reacted with bodily fluids to form hydroxyapatite ($Ca_{10}(PO_4)_6(OH)_2$), although the hydroxyapatite was not necessarily stoichiometric. The XRD peaks are smaller in the pattern for the Cu-3 glass than those in the pattern for the 13-93B3 glass because the addition of copper slowed the HA formation kinetics, and since the crystals may still be in the process of fully crystallizing, the crystals are smaller and therefore less detectable, or possibly a combination. Either way, it is significant that the Cu-3 glass formed a material that when X-rayed had HA peaks of lower intensity than those for the 13-93B3 glass. Raman spectroscopy of reacted B3 Cu-3 and B3 CS fibers as discussed further below indicated that a carbonated form of hydroxyapatite known as HCA was present. The B3 CSZ glass reacted to form what appeared to be a multi-phase mixture of hydroxyapatite and calcium carbonate (calcite). The XRD patterns of the reacted B3 CSZF scaffolds contained larger peaks for calcite only. This is believed to be the first documented instance known to the inventors where any type of a calcium-containing glass implanted in an animal has reacted to form calcite or any other material other than HA/HCA.

Example 4

Figure 5:
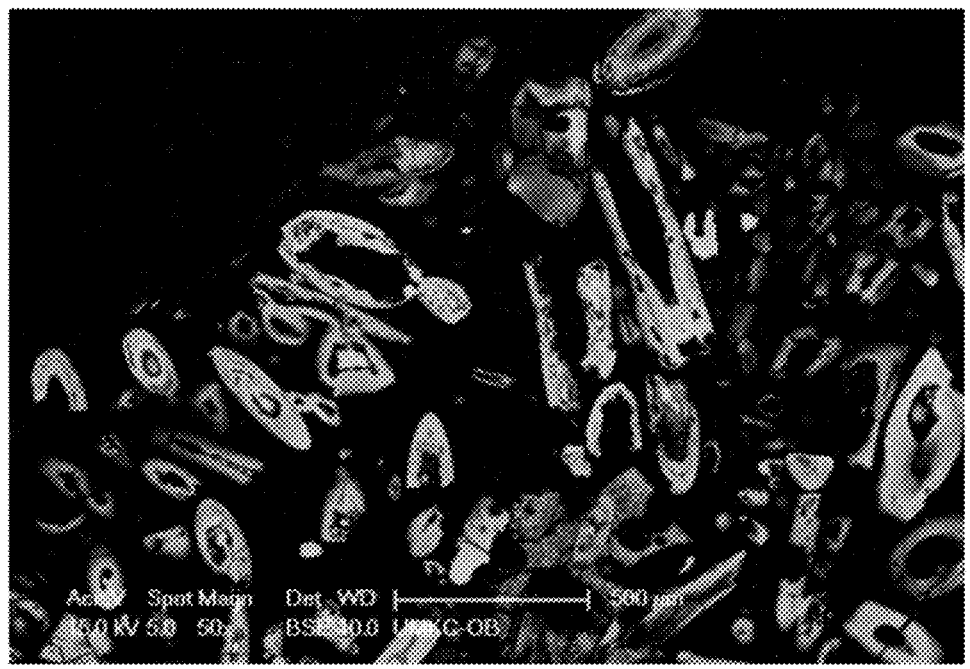
FIG. 5 is an SEMBSE image of a cross sectioned Cu-3 fiber scaffold that was implanted in the subcutaneous tissue of a rat for six weeks.
Figure 6:
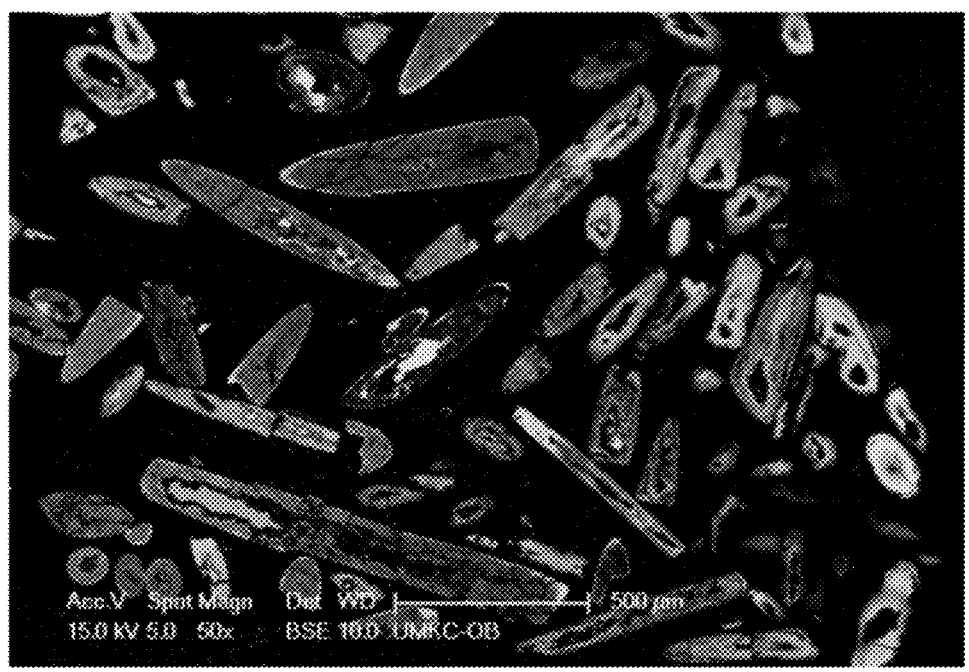
FIG. 6 is an SEMBSE image of a cross sectioned CS fiber scaffold implanted subcutaneously in the back of a rat for six weeks.
Figure 7:
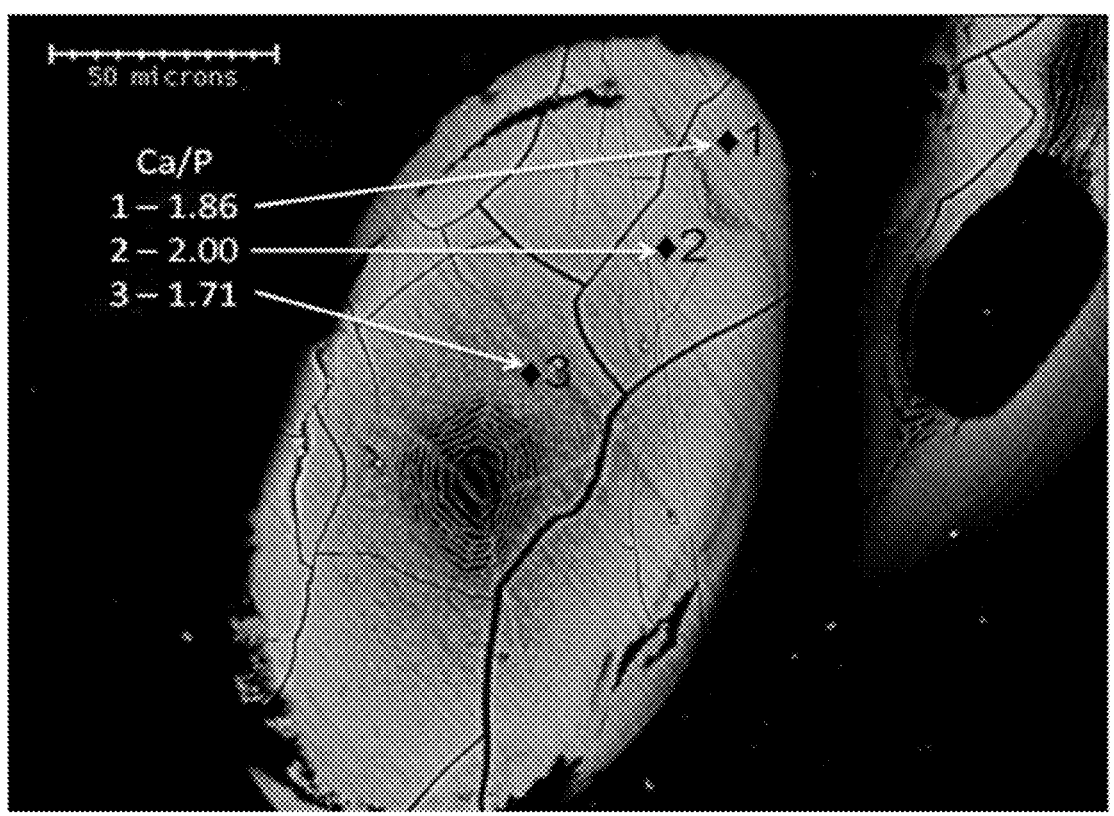
FIG. 7 is an SEMBSE image of a CS fiber implanted subcutaneously in the back of a rat for six weeks.

Cross sections of the various scaffolds after removal were prepared and examined. FIG. 5 is an SEMBSE image of the B3 Cu-3 scaffold (borate glass doped with Cu) after six weeks in subcutaneous tissue. All of the as-made borate glass fibers have reacted with the bodily fluids to form hydroxyapatite, see FIG. 4, and as a consequence, most of the fibers have become partially excavated. The hollowing effect is caused by the glass containing too little calcium to form enough hydroxyapatite upon reaction with the phosphate present in the bodily fluids to form a solid fiber. A similar reaction product, hydroxyapatite, is present in the SEMBSE of the borate B3 CS glass (doped with Cu plus Sr) in FIG. 6 and the reacted fibers are again mostly hollow. A reacted fiber from the B3 CS scaffold was chosen for compositional analysis, and is shown in FIG. 7. The chemical composition was measured at the three numbered spots across the fiber in FIG. 7, and SEMEDS spectra generated for analysis. The Ca/P molar ratio of the material at the three numbered spots is shown in the figure. Except for trace amounts of Na, Mg, and K; Ca and P were the major components at each spot and the similarity in the peak height for each in the spectra revealed that the chemical composition of the reacted fiber is similar from the center (point 3) to the outer surface (point 1). The XRD data in FIG. 4 indicate that the initially glass fibers had converted to HA.

Figure 8:
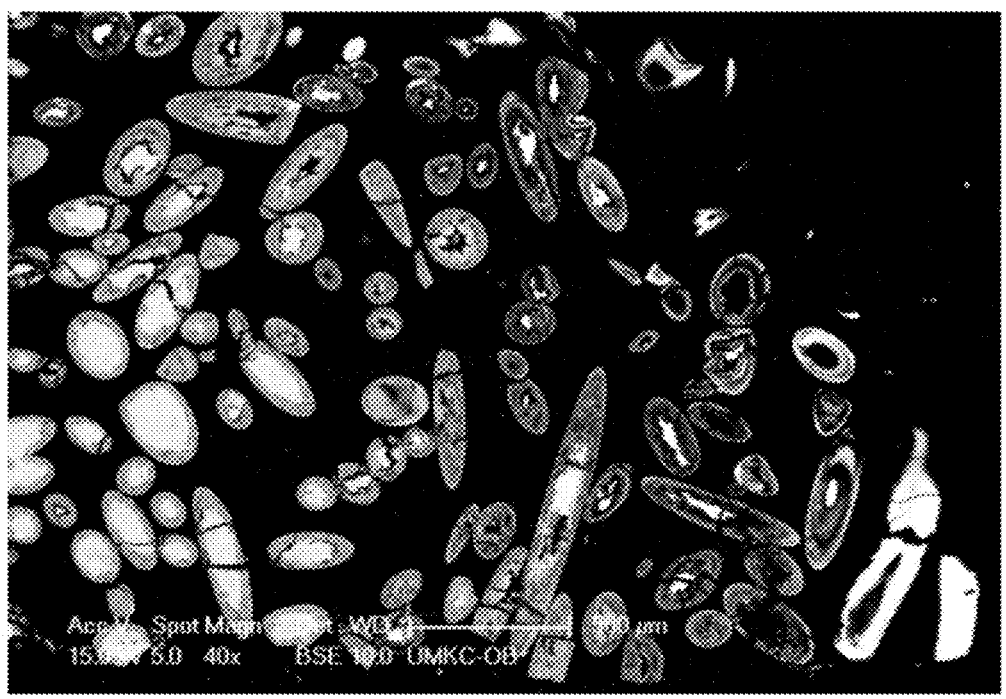
FIG. 8 is an SEMBSE image of a cross sectioned CSZ fiber scaffold implanted subcutaneously in the back of a rat for six weeks.
Figure 9:
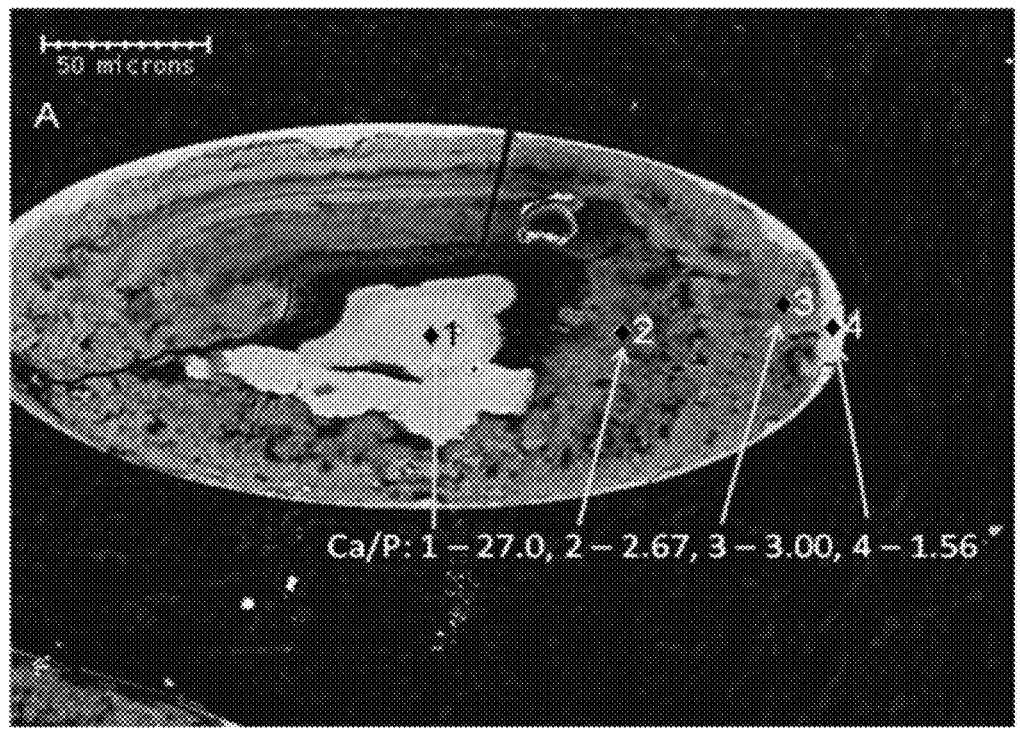
FIG. 9 is an SEMBSE image of a cross sectioned CSZ fiber scaffold implanted subcutaneously in the back of a rat for six weeks.

The SEMBSE image of a scaffold made from B3 CSZ fibers (doped with Cu, Sr, and Zn), is shown in FIG. 8. Some of the larger diameter fibers in the lower left side of the image, which have a white material in the center have not fully reacted with the bodily fluids. The white core is composed of the unreacted B3 CSZ glass. The fibers at the outer edge of the scaffold (right center and side) are fully reacted but not hollow as were the B3 Cu-3 and B3 CS fibers. A relatively small region of a calcium containing material is present at the center of the B3 CSZ fibers. This is better illustrated by the fiber in FIG. 9, where three distinct layers of material are visible. The composition at the four numbered spots across the fiber was measured by SEMEDS. At spot 1 (center) only calcium and oxygen were detected along with trace amounts of Mg, and K. Carbon may have been present, but is undetectable by SEMEDS, so this material is consistent with being $CaCO_3$ as found by XRD, see FIG. 4. The SEMEDS spectra at spots 2 and 3 contained peaks for both calcium and phosphorus with an intensity ratio similar to that of hydroxyapatite. Spot 4 (at the outer edge) contained both calcium and phosphorus and had the highest signal among spots 2, 3, and 4. The SEMEDS and XRD results indicate that a relatively dense layer of HA at the outer surface (spot 4) surrounds a more porous and layered hydroxyapatite-like material at spots 3 and 2, and the white, calcium rich, material at the core, spot 1, is most likely calcium carbonate (calcite).

Figure 10:
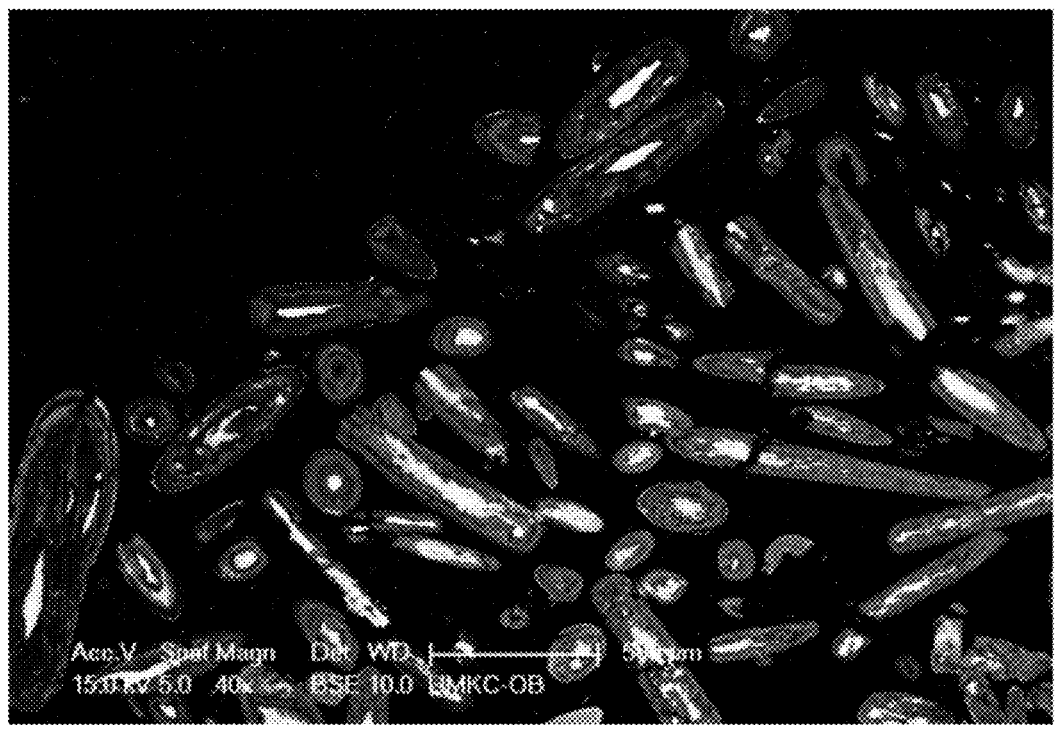
FIG. 10 is an SEMBSE image of a cross sectioned CSZF fiber scaffold that was implanted subcutaneously in the back of a rat for six weeks.
Figure 11:
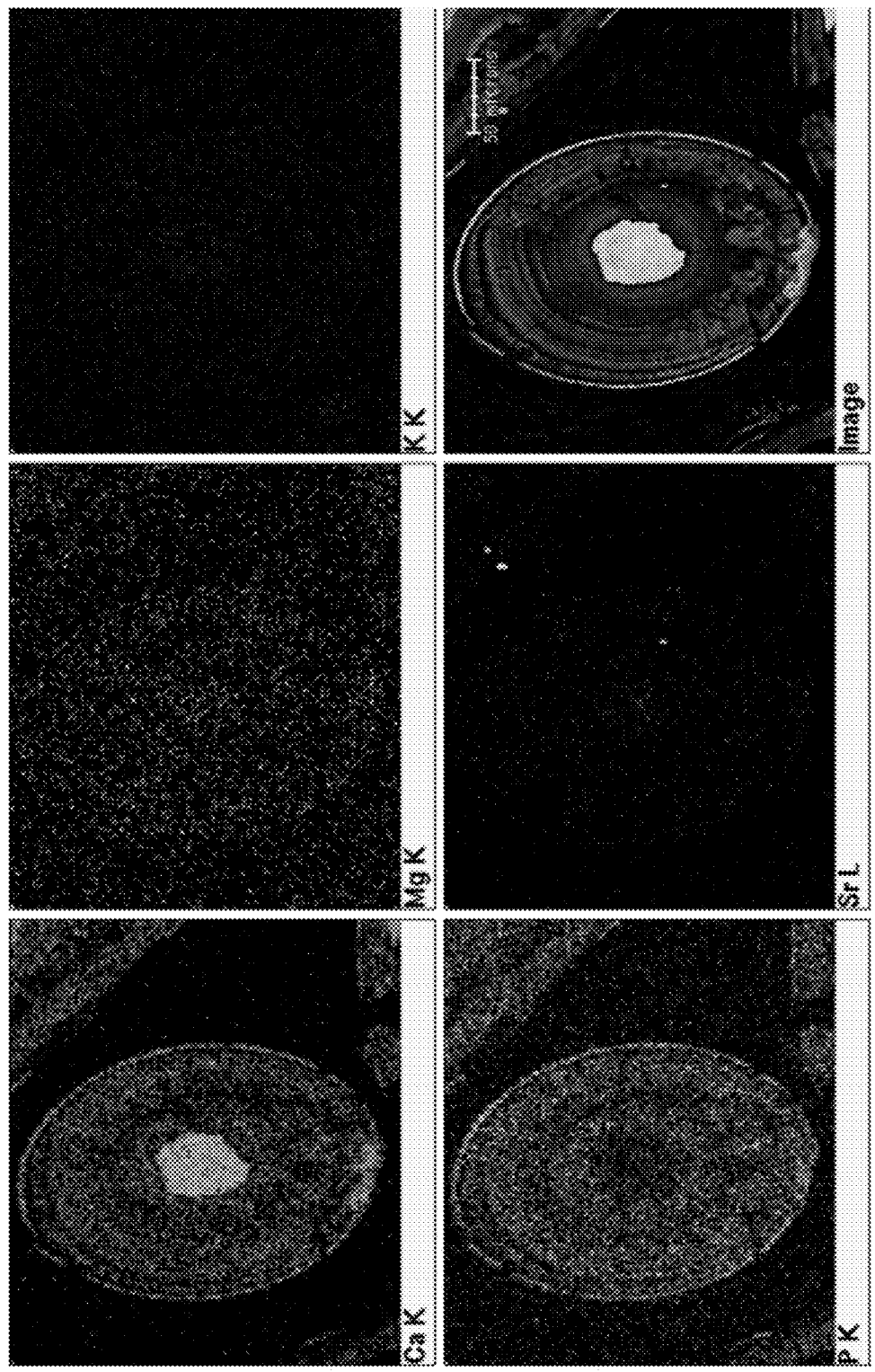
FIG. 11 is an EDS phase map of CSZF reacted fiber after six weeks in rat subcutaneous tissue. The SEMBSE image is shown bottom right of the image for reference.
Figure 12:
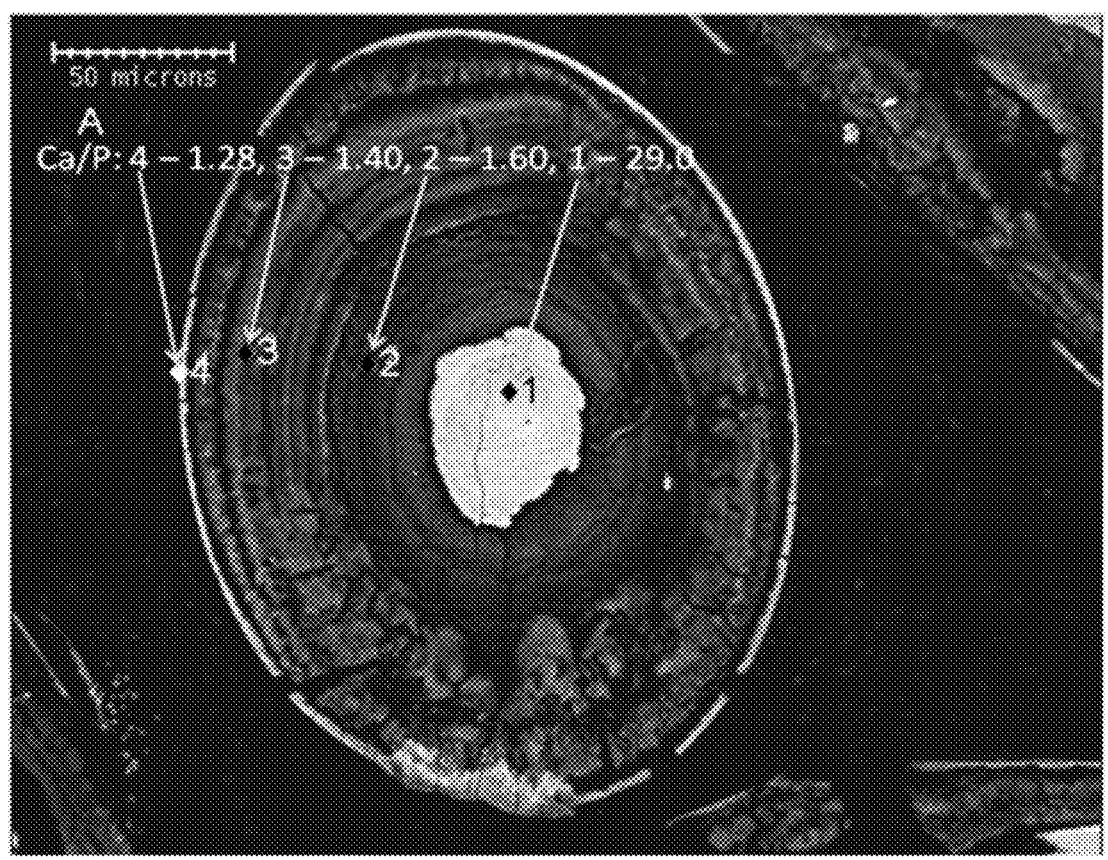
FIG. 12 is an SEMBSE image of a CSZF fiber implanted subcutaneously in the back of a rat for six weeks.
Figure 13:
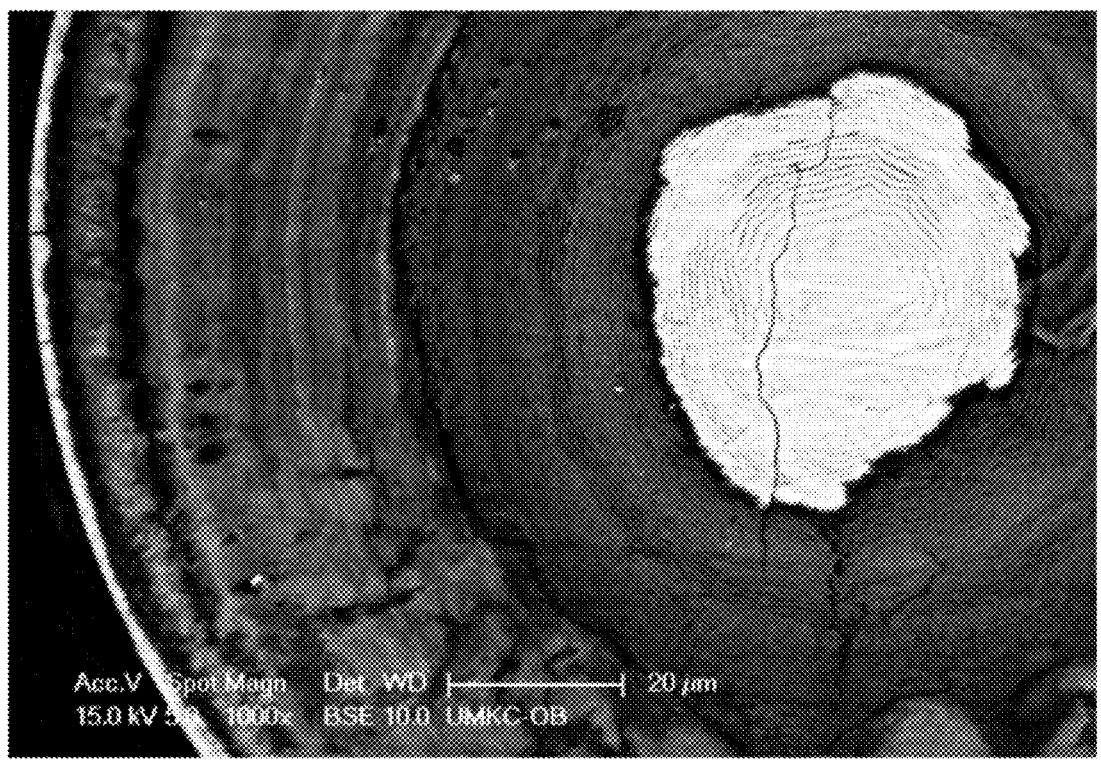
FIG. 13 is a higher magnification photograph of the image in FIG. 12.

The SEMBSE image in FIG. 10 of the B3 CSZF scaffold, made from fibers doped with Cu, Sr, Zn and Fe shows a cross section of reacted fibers with a hydroxyapatite outer layer and a calcium-rich core (lighter material) similar to that shown for the B3 CSZ scaffold in FIG. 8. The image in FIG. 10 however shows there is significantly more calcium present within the reacted fibers than in FIG. 8. The larger amounts of calcium present in the B3 CSZF scaffold are evident both visually in the SEM images in FIGS. 8 and 10 and by the height (size) of the peaks in the XRD patterns in FIG. 4 which provide a positive identification that the material is calcium carbonate, calcite. Verification that the calcium-rich core in the B3 CSZF glass was calcite and free of phosphate is provided by the SEM phase map for the reacted B3 CSZF fiber, shown in FIG. 11. Calcium is present throughout the fiber, in what is believed to be hydroxyapatite-like material and presumably calcium carbonate. However, the largest concentration of calcium is at the core as indicated by the bright spot in the upper left of FIG. 11. There are only low levels of Mg, Sr, and K in the fiber indicating that the glass has significantly reacted and most of the elements have been released to the bodily fluids. Phosphorus is present in the outer portions of the fiber but there is a distinct area devoid of phosphorus in the center of the fiber at the same area of highest calcium concentration, which means there is no calcium phosphate present. SEM EDS at four spots across the same fiber in FIG. 12 show a similar reaction product as that present in the B3 CSZ fibers. There is a thin outer layer (1-2 micron) of dense hydroxyapatite (spot 4), a region of porous and layered hydroxyapatite (spots 2 and 3), and a calcium rich core (spot 1) as indicated by the relative intensity of the SEMEDS peaks. The fiber reacted with bodily fluids and formed a distinctly different material at the center (white). The Ca/P molar ratio was measured with SEMEDS at the four numbered spots indicated. As shown in FIG. 13, at higher magnification, the reacted calcium-rich core (white center) had a similar layered structure as that of the surrounding hydroxyapatite, which is formed as the glass reacts with bodily fluids. The reaction of the borate glass fibers with the bodily fluids starts at the external surface of the fiber and proceeds inward.

Example 5

Figure 14A:
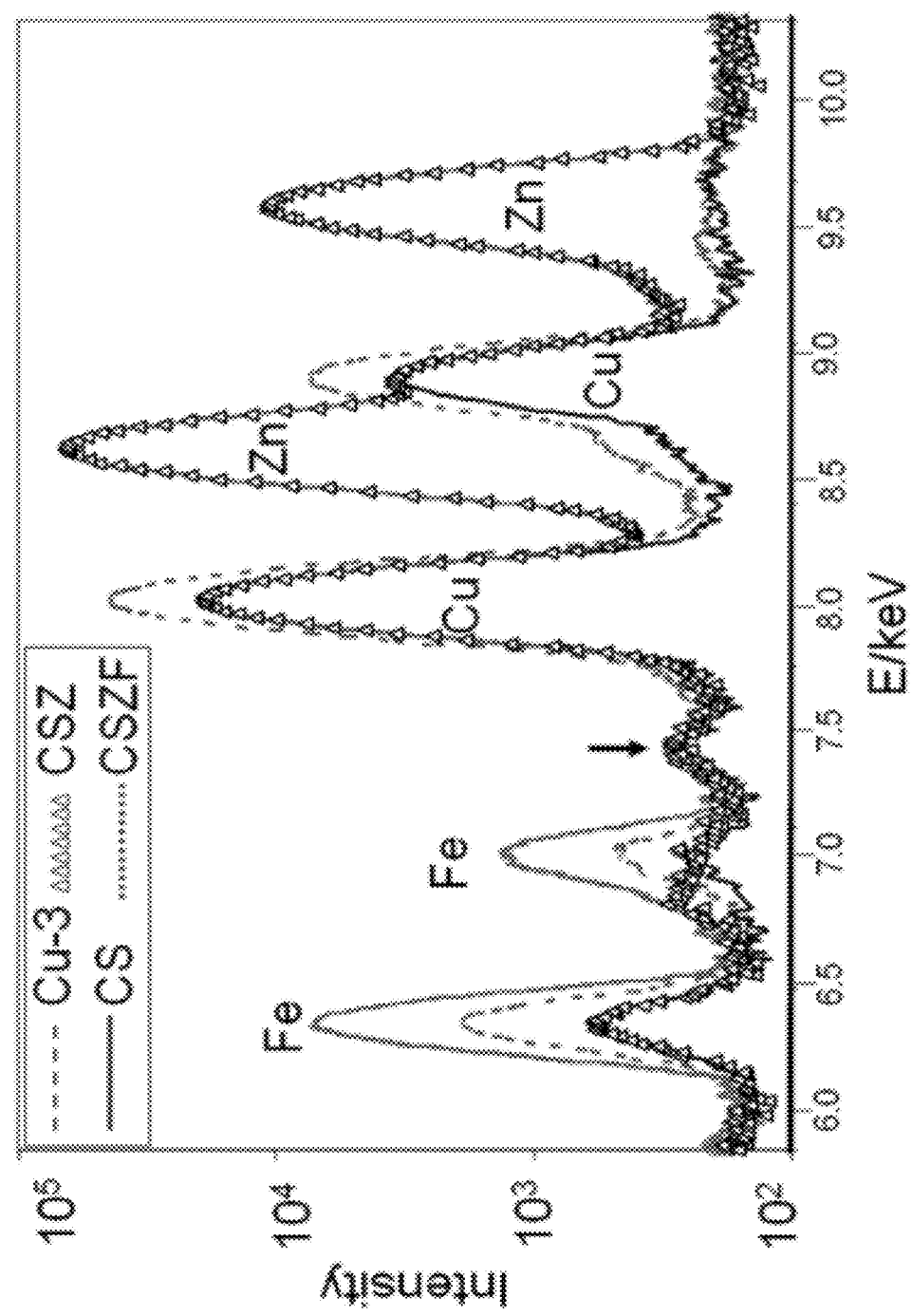
FIGS. 14 and 15 are XRF patterns of compositions of the invention as-made and after implantation in vivo.
Figure 14B:
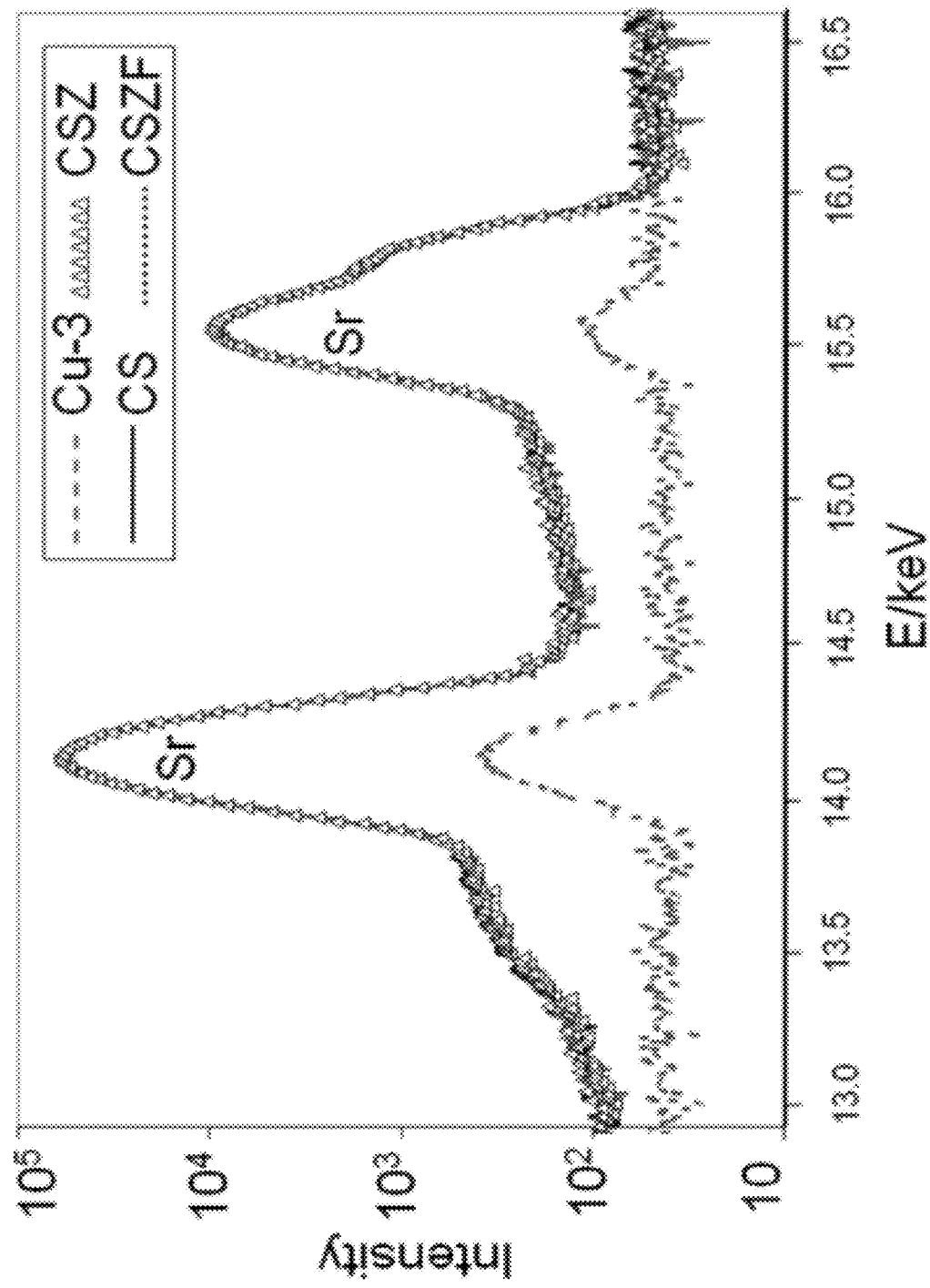
Figure 15A:
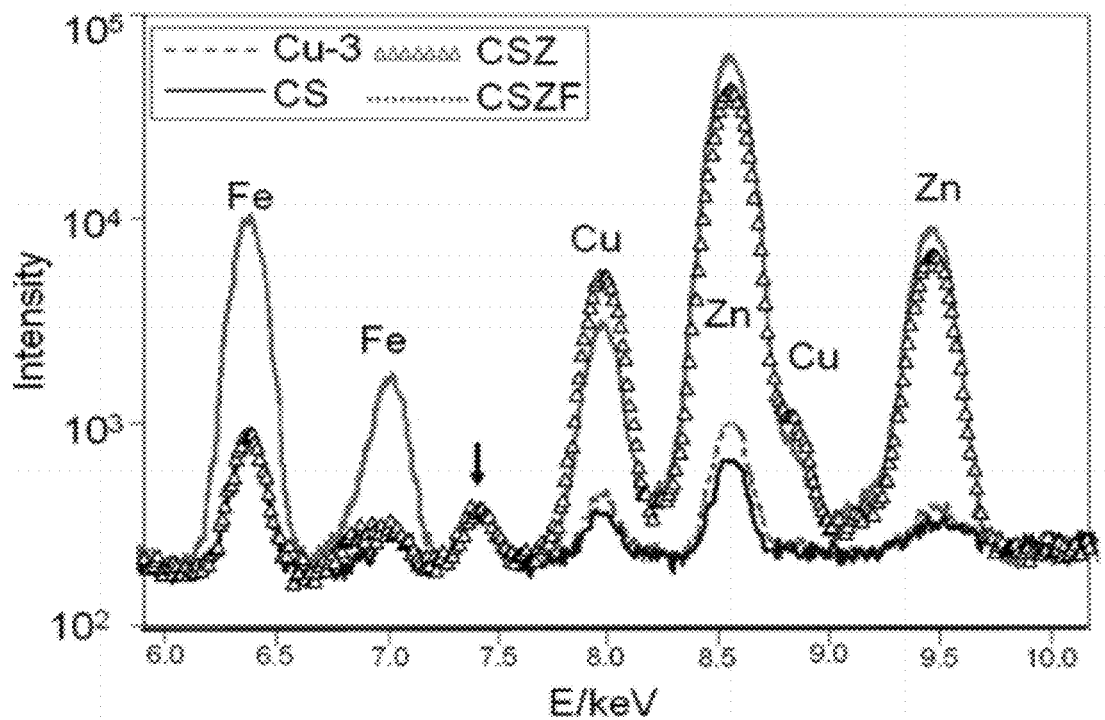
Figure 15B:
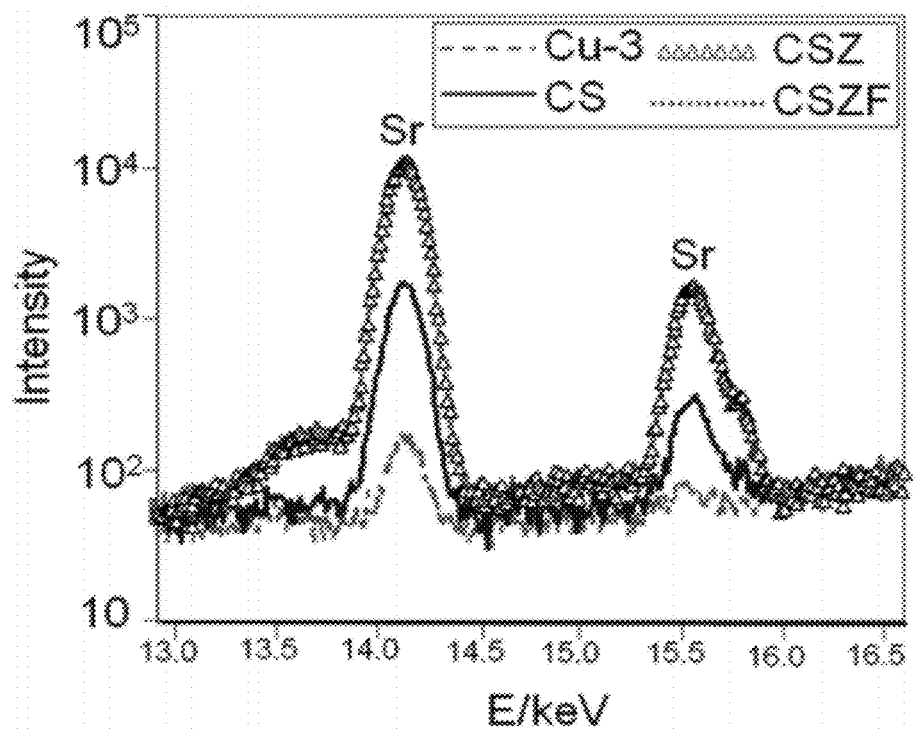

To determine the role the minor director elements played in the conversion reaction of the scaffolds, x-ray fluorescence (XRF) was used to measure the composition of the as-made glass and the scaffolds reacted in vivo. The as-made glass was measured to verify the presence of the minor elements in the as-made glass, and to ensure the relative concentrations of the minor elements were similar. The XRF patterns for the minor elements of interest (Cu, Sr, Zn, and Fe) for the four glasses are shown in FIGS. 14A and 14B. All four minor elements (Cu, Sr, Zn, and Fe) were present in the as-made glasses (prior to implantation). The concentrations of Cu were similar in all four of the as-made glasses as expected, and the Zn concentration was essentially identical in the two glasses to which it was added. The arrow in 14A indicates a peak associated with the polymer mounting material. A scaffold of each type seeded with mesenchymal stem cells was analyzed to determine if the minor elements (Cu, Sr, Zn and Fe) were detectable in the scaffold of soft tissue after the in vivo reaction. The XRF patterns shown in FIGS. 15A and 15B are for scaffolds after six weeks in vivo, and all four minor elements were detected in either the reacted fibers or the new soft tissue. The Sr was weakly detectable in the HA layers from the SEMEDS phase map in FIG. 11; but the other minor elements (Cu, Zn, Fe) were of too low concentration to determine if they were present in the HA layer by SEMEDS. The arrow in 15A indicates a peak associated with the polymer mounting material. The XRF data in FIGS. 15A and 15B proves that at least some of the minor elements were present in the reacted scaffold or soft tissue adjacent to the fibers and not completely removed by bodily fluids, which may explain why the fibers reacted differently and calcium carbonate instead of HA was formed in the B3 CSZ and B3 CSZF fibers.

The contrast in color, or shading, of the SEMBSE images between the B3 CS fiber and the B3 CSZF fiber along with the hollow nature of the B3 Cu-3 and B3 CS fiber versus the partially filled B3 CSZ and B3 CSZF fibers, with a calcium rich core, points to a change in how the glasses react with the bodily fluids and how calcium is potentially blocked from reacting with the phosphate in the bodily fluids. The hollow core of a reacted fiber or particle has been previously described as what occurs in a glass which does not contain enough calcium to form a fully dense structure composed of HA. The B3 CS and B3 CSZF glasses had an almost identical amount of calcium present and formed completely different structures when they reacted in vivo in an identical environment. The combination of minor elements with those already present in the glass caused a change in the bonding between the calcium and phosphorus which made a more porous structure of hydroxyapatite followed by the deposit of a calcium rich core.

With additional compositional modifications, it should be possible to completely block the formation of hydroxyapatite and form other calcium containing compounds (phosphates, carbonates, hydrates, fluorides, etc.). Other combinations of minor elements may make it possible to form compounds other than hydroxyapatite or calcium carbonate, and make new multicomponent reaction products similar to those described above. Mixing fibers of different compositions that form different reaction products as a blended scaffold offers a way to make an entirely new family of degradable materials that are biocompatible. These reaction products are potentially useful in drug delivery or bone or other soft tissue regeneration.

Example 6

Figure 16:
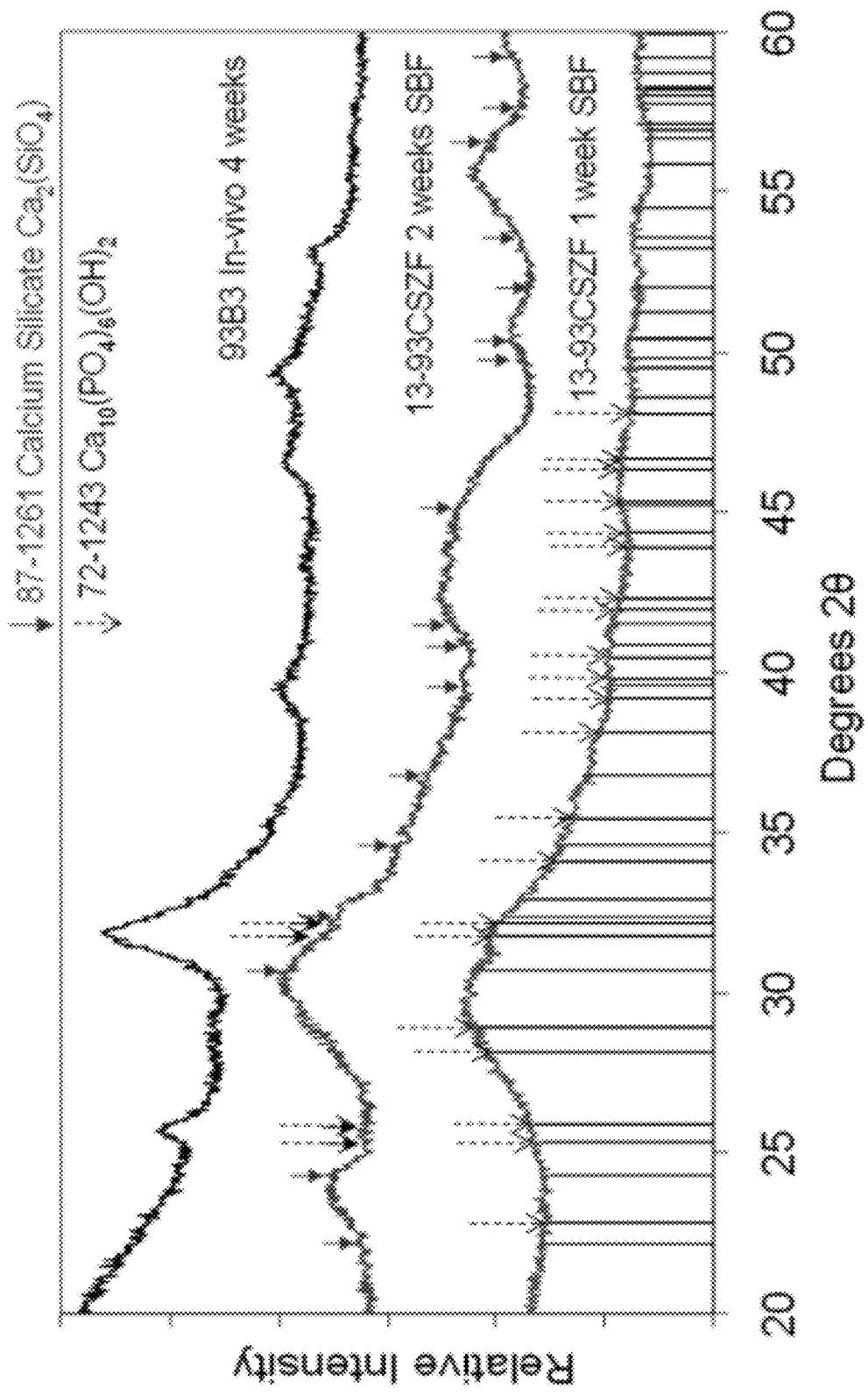
FIG. 16 is an XRD pattern of a composition of the invention after one and two weeks in simulated bodily fluids.

A silicate based bioactive glass 13-93 was modified similarly to that of 93B3 glass by adding small amounts of Cu, Sr, Zn, and Fe according to the composition of 93-CSZF in the foregoing table. The glass was melted, plate quenched, and crushed to a particle size range of 150 to 300 microns. The particles were immersed in simulated bodily fluid for up to 2 weeks at 37° C. and x-rayed for phase identification. After 1 week in simulated bodily fluids, relatively broad XRD peaks were present as shown by the bottom pattern in FIG. 16, but no crystalline phases could be identified. In the XRD pattern at 2 weeks (middle pattern in FIG. 16) small, barely detectable XRD peaks corresponding to HA (black arrows) were present when compared to the top pattern above which is for a bioactive borate glass reacted in vivo. The large peaks at ~24 and 31 degrees 2θ are not associated with HA, but match well with $Ca_2SiO_4$. There are several other smaller peaks that match the standard XRD pattern for $Ca_2SiO_4$ and those peaks are indicated by the arrows in FIG. 16. Assuming the four minor elements in the glass prevent the formation of calcium with phosphate to form a HA type phase as in the borate glasses described earlier, the calcium would be free to bond with the silica to form a calcium silicate compound such as $Ca_2SiO_4$. The formation of a material other than HA in a bioactive silicate glass is important because this means that the addition of minor elements can be used in either silicate or borate glasses to control or alter the reaction products that form when in contact with bodily fluids or simulated bodily fluids and different materials having desired properties can be made on demand by this method of adding minor elements.

Example 7

Micro Raman analysis was performed on glasses of the invention and glasses not of the invention to investigate what compounds are formed in vivo.

Figure 17:
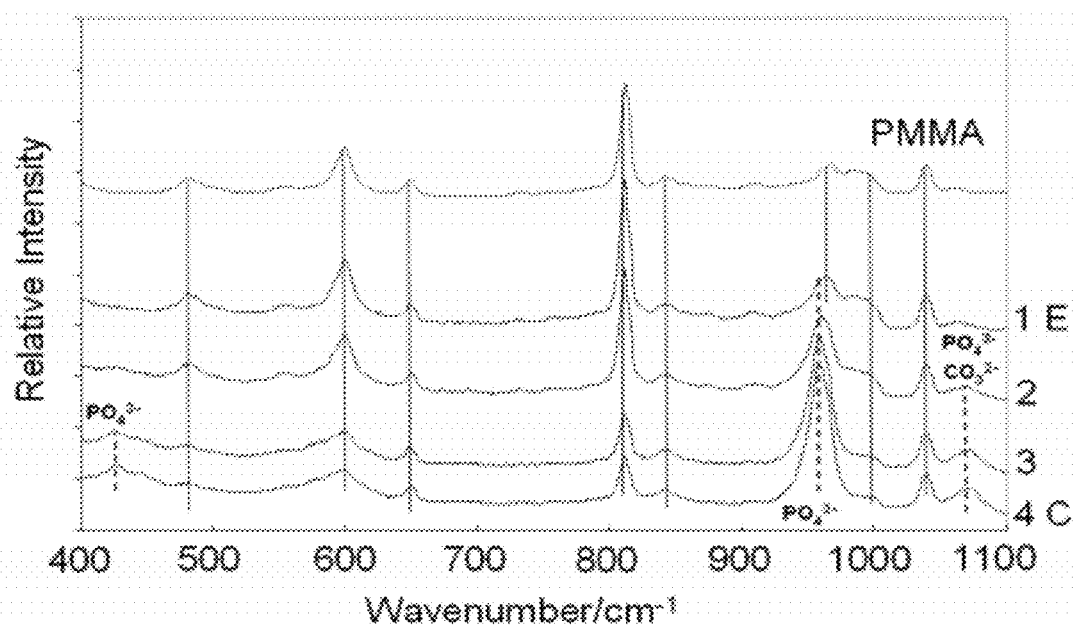
FIGS. 17-23 are micro Raman spectra of compositions of the invention as described in Example 7.

A reacted 13-93B3 fiber of the composition described in Example 1 (reacted four weeks in vivo) was analyzed by micro raman at four locations, and the micro-raman spectra for the four spots are shown in FIG. 17. Spot one is located at the outer edge of the fiber and spot four at the center of the reacted fiber. The peaks associated with HA (431 cm$^{-1}$ ($PO_4^{3-}$ v2), 965 cm$^{-1}$ ($PO_4^{3-}$ v1), 1065 to 1070 cm$^{-1}$ ($CO_3^{2-}$ v1) and 1076 cm$^{-1}$ $PO_4^{3-}$ v3) are denoted by dashed lines. The solid lines indicate peaks due to the PMMA mounting medium as demonstrated by the spectrum shown at the top of FIG. 17.

Spots three and four located near the center of the reacted 13-93B3 fiber have the highest intensities for the phosphate and carbonate peaks of the four spots analyzed, indicating there may be a difference in the amount of each species distributed throughout the reacted layers. The difference in the measured amount of phosphate and carbonate measured could also be due to density differences of the reacted fiber, especially at the center with the layered microstructure. The difference in the phosphate and carbonate concentration may also indicate that the fiber is not completely converted. The presence of a carbonate peak at 1065 to 1070 cm$^{-1}$ ($CO_3^{2-}$ v1) indicates that the reacted fibers are carbonated, similar to natural bone. The significance of this analysis is the presence of hydroxyapatite and the absence of calcite in this prior art glass containing borate as the primary glass former, and also containing $Na_2O$, CaO, $K_2O$, MgO, and $P_2O_5$.

Figure 18:
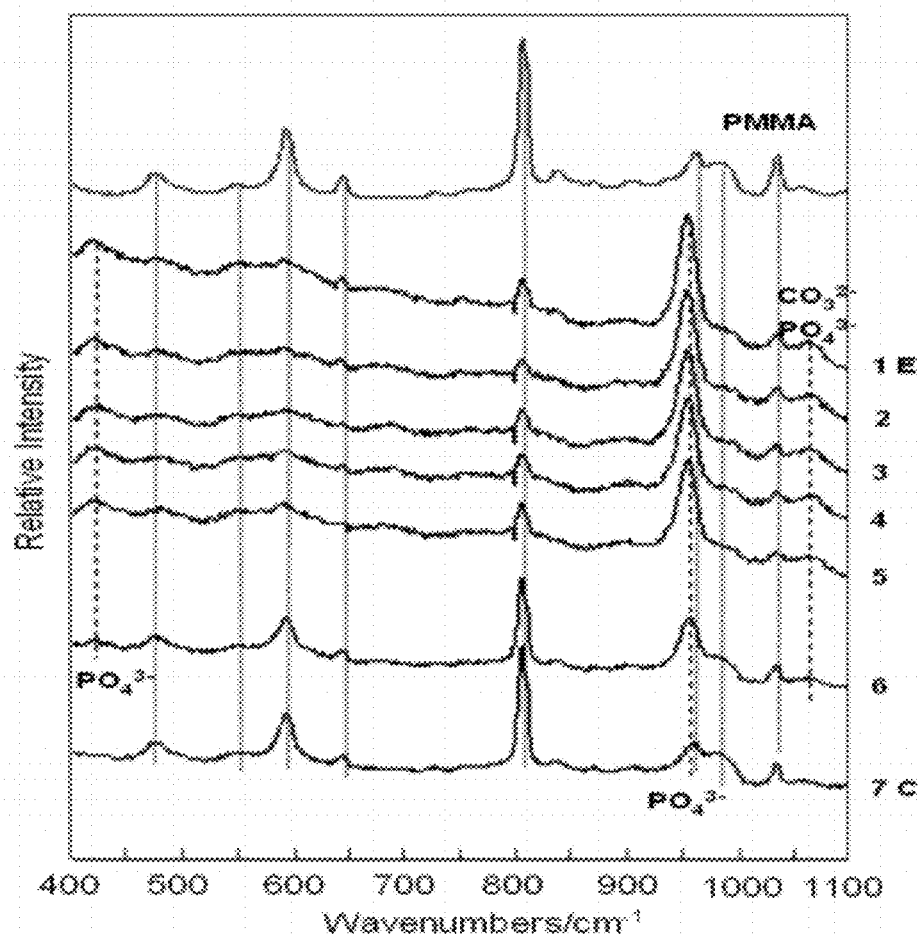

Micro Raman analysis of a Cu-3 fiber (Example 1) after six weeks in vivo was performed at seven spots across the cross section of a reacted fiber from its outer edge to its center. See FIG. 18. The majority of the peaks in the Raman spectra are due to the PMMA in which the scaffold is mounted. The peaks important for identifying HA are located at 431 cm$^{-1}$ ($PO_4^{3-}$ v2), 965 cm$^{-1}$ ($PO_4^{3-}$ v1), 1065 cm$^{-1}$ and 1070 cm$^{-1}$ (CO$_3^{2-}$ v1), and 1078 cm$^{-1}$ (PO$_4^{3-}$ v3). The intensity of the HA peaks in spectra one to five are almost identical indicating no significant change in the material from the outer edge to the center. The PO$_4^{3-}$ v2 and PO$_4^{3-}$ v3 peaks in spectra six are noticeably lower than the corresponding peaks in spectra one to five. There was also an increase in the intensity of the PMMA peak at 600 cm$^{-1}$ in spectra six indicating a higher porosity of the fiber at its center. The presence of CO$_3^{2-}$ peaks are the first evidence that the HA is carbonated similar to natural bone.

Figure 19:
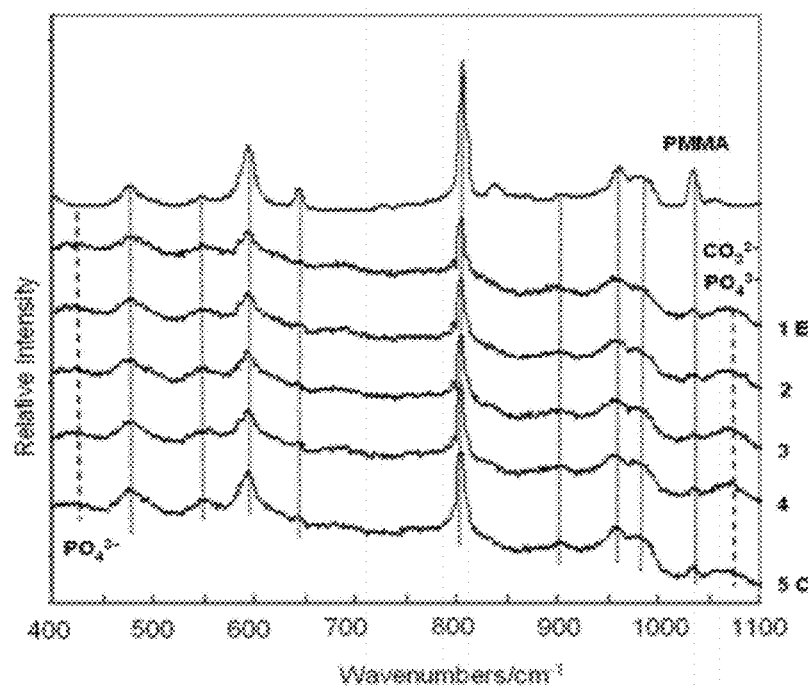

FIG. 19 shows micro Raman spectra of a CS fiber (Example 1) after six weeks in vivo at five spots across the fiber from its outer edge to its center. The only peaks associated with HA are located at 428 cm$^{-1}$ (PO$_4^{3-}$ v2) and the broad peak at 1065-1080 which encompasses 1065 and 1070 cm$^{-1}$ (CO$_3^{2-}$ v1), and 1078 cm$^{-1}$ (PO$_4^{3-}$ v3). The 965 cm$^{-1}$ (PO$_4^{3-}$ v1) peak for HA was not seen in any of the spectra in FIG. 19.

Figure 20:
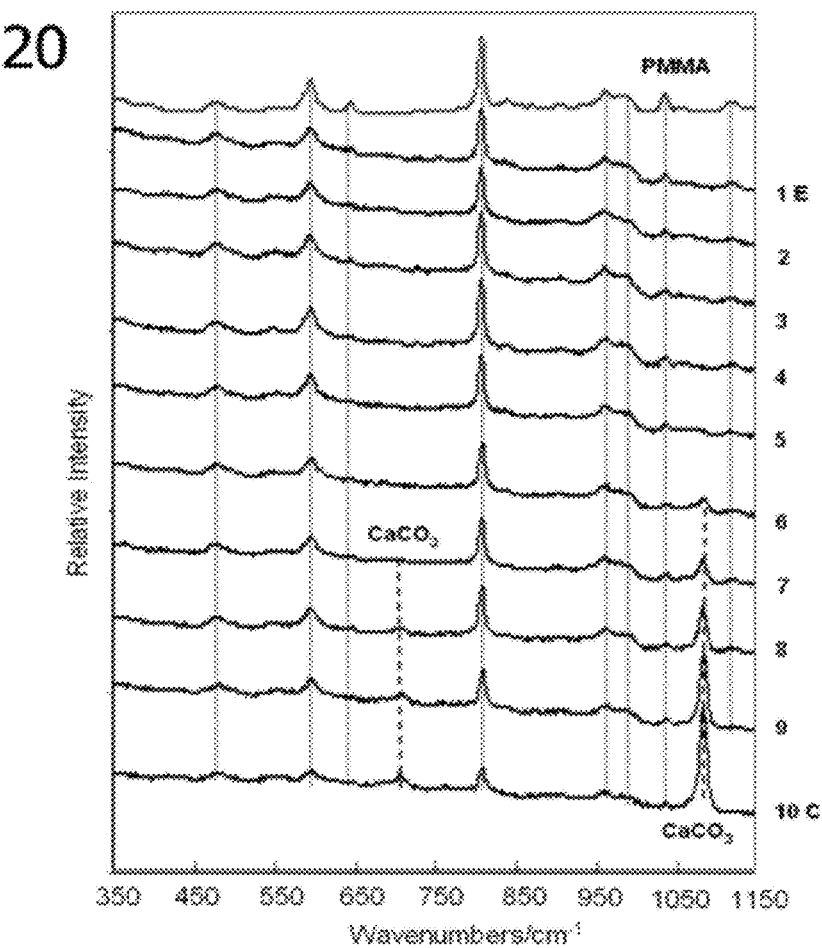
Figure 21:
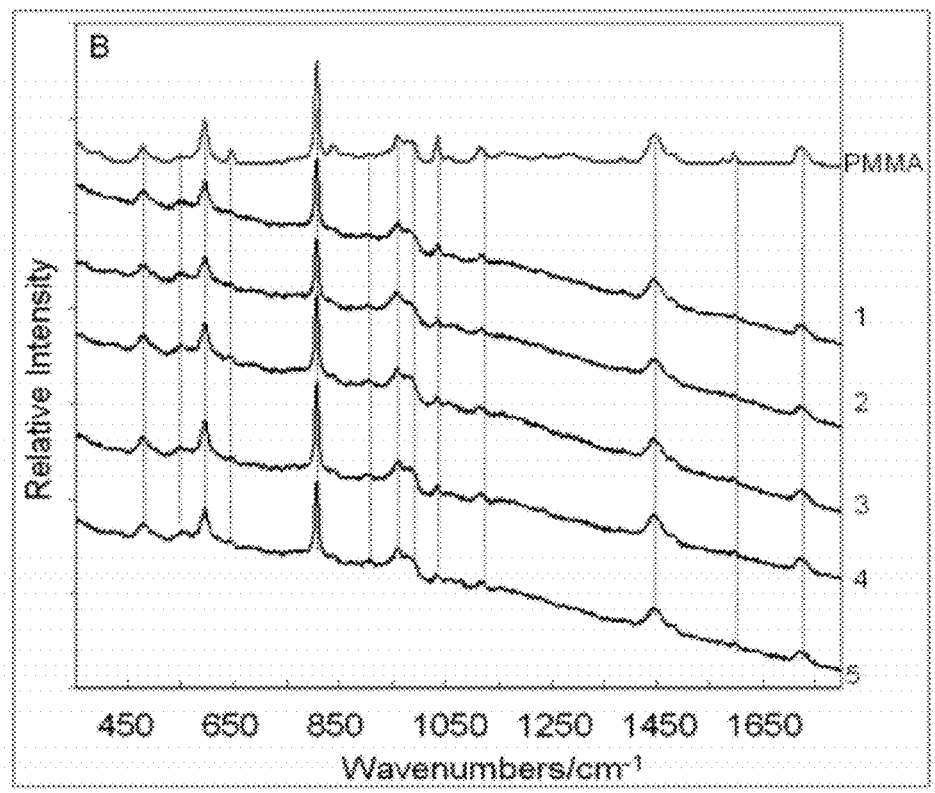
Figure 22:
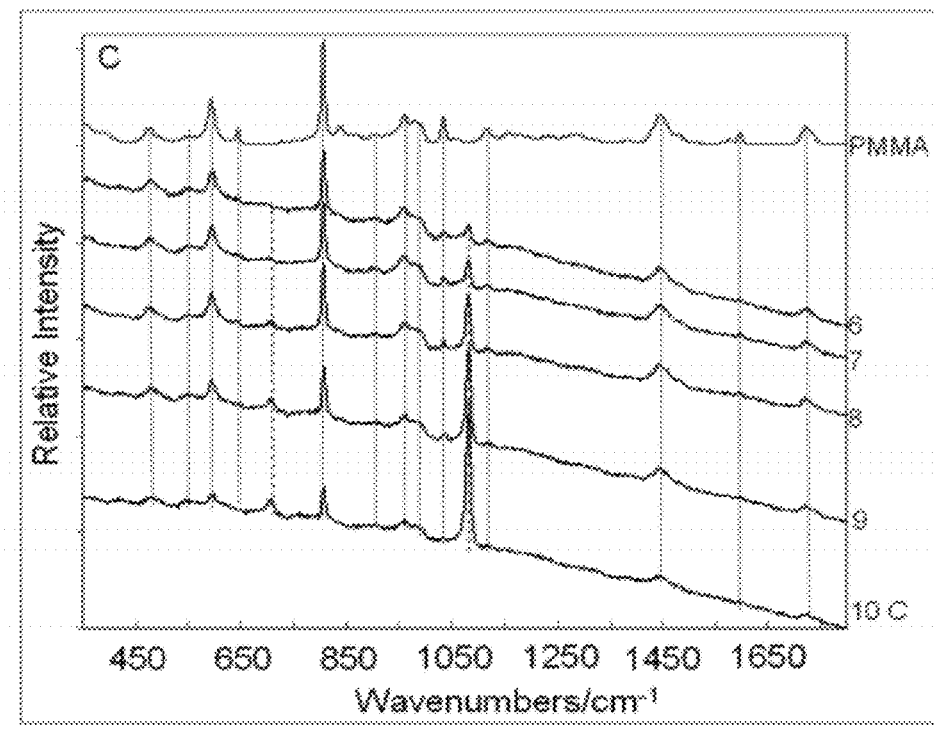

FIG. 20 shows the ten spots analyzed by micro Raman spectroscopy of a CSZ fiber (Example 1) after six weeks in vivo from its outer edge to its center. The first five spectra in FIG. 21 are from the outer edge to up to the interface between the porous calcium phosphate and the calcium rich center. No peaks associated with HA are present in the micro Raman spectra for spots one to five. The spectra for the calcium rich center in FIG. 22 contain two peaks at 711 cm$^{-1}$ and 1085 cm$^{-1}$ in spectra 6 to 10 and these peaks are associated with calcium carbonate in the form of calcite.

Figure 23:
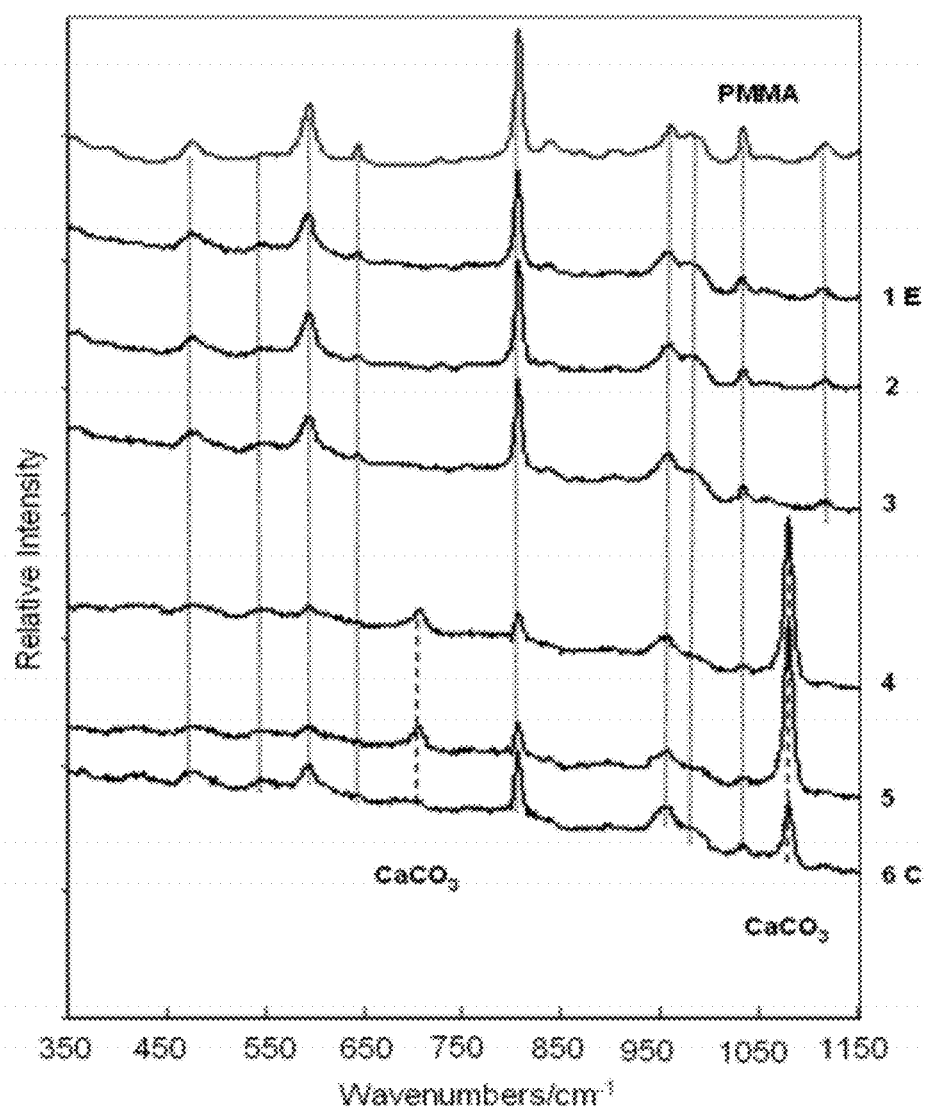

FIG. 23 shows the six spots analyzed by micro Raman spectroscopy for a CSZF fiber (Example 1) after six weeks in vivo, from its outer edge to its center. No peaks associated with HA were present in any spots analyzed. The peaks at 711 cm$^{-1}$ and 1085 cm$^{-1}$, attributable to calcite, were present once inside the calcium rich center at spots four to six.

In summary, analysis of the reacted fibers showed that the majority of un-doped fibers were fully converted to hydroxyapatite after four weeks. The addition of the minor elements affected the conversion of the bioactive glass scaffolds to hydroxyapatite. The scaffold containing copper converted to HA, but a slower rate than the base glass without copper. The combination of copper and strontium significantly retarded the reaction of the phosphate in the bodily fluids with the calcium released from the borate glass as determined by micro Raman measurements, but a highly porous HA had formed instead according to XRD. The addition of zinc to the copper and strontium doped borate glass effectively stopped the formation of calcium phosphate (HA) toward the center of the fibers and formed calcium carbonate in the form of calcite formed instead. When iron was added to a glass doped with copper, strontium, and zinc the formation of calcium phosphate (HA) was decreased even further as the calcite present at the center of the reacted fibers continued to increase. This is believed to be the first time calcium containing bioactive glasses were documented to transform to materials other than calcium phosphates in vivo.

The foregoing data show a progressive change in the reaction of borate glasses with the bodily fluids of a rat. With the addition of the minor elements, such as Cu, Sr, Zn, and Fe, to a borate glass, the formation of HA ceases and eventually only calcium carbonate is formed. The elements that had the largest effect on the conversion of the glass to HA were zinc and iron. The XRD first peaks for calcite appeared in the CSZ (Ca, Sr, Zn) scaffold, and when a small amount of Fe was added to that composition, HA could not be detected by XRD, and only calcite was detectable.

Figure 24:
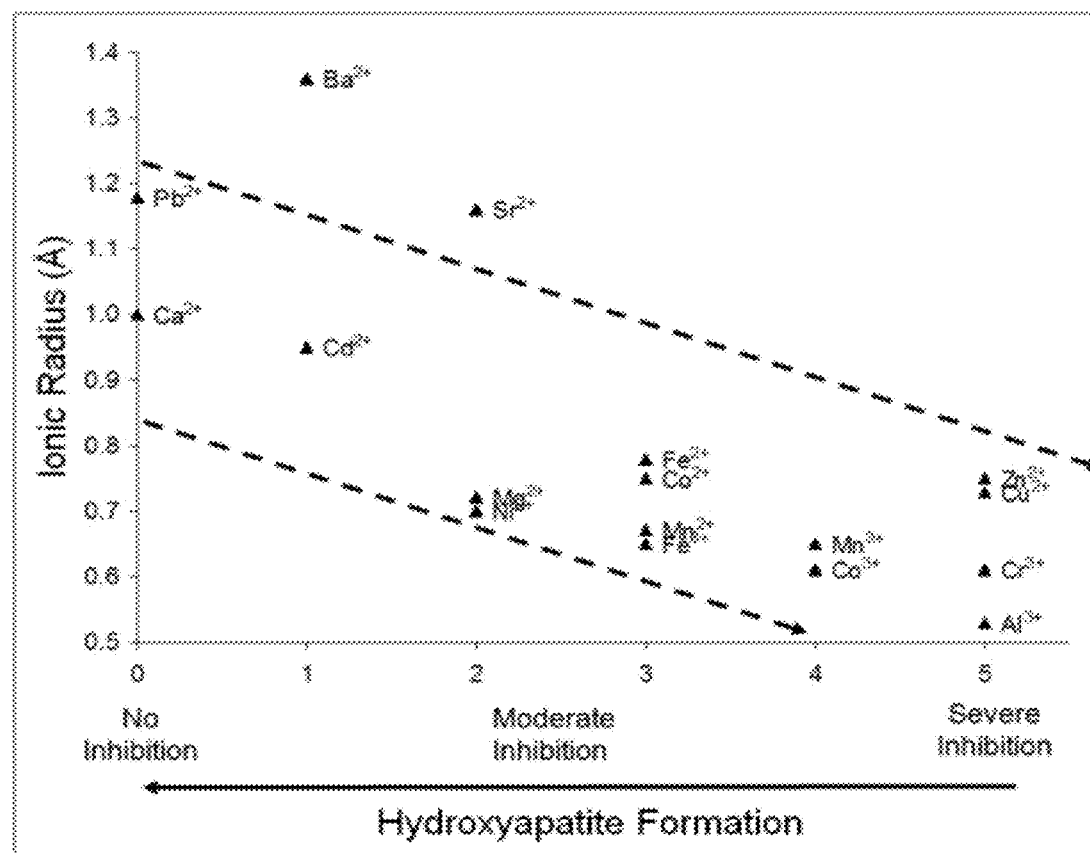
FIG. 24 is a schematic presentation of how hydroxyapatite formation is inhibited by the presence of six coordinated ions in aqueous environments.

As noted above, calcium-containing implantable bioactive glasses form hydroxyapatite upon reaction with bodily fluids. In accordance with this invention, the glass composition is formulated to include the one or more director elements so as to produce calcium compounds other than hydroxyapatite. In some embodiments, these other calcium compounds are formed entirely instead of hydroxyapatite. In other embodiments, a mixture of hydroxyapatite and one or more other calcium-based compounds is formed. In one preferred embodiment of the invention, the implantable glass composition is formulated to promote the formation of calcite upon reaction with bodily fluids in vivo. Without being bound to a particular theory, it appears the ionic radius of a particular element has an impact on its efficacy as a director element alone or in combination with other elements in accordance with this invention. In particular, it is believed that an element with a relatively smaller ionic radius such as less than about 1 angstrom, or on the order of 0.8 angstroms or less, provides moderate to severe inhibition of hydroxyapatite formation, and biases the system toward calcite formation. FIG. 24 is a schematic graph showing relative inhibition of hydroxyapatite in the presence of six coordinated ions in aqueous environments.

Calcite is a polymorph of calcium carbonate that can be found in nature in both seashells and coral. Calcite has been used as a degradable scaffold material and has been shown to promote bone marrow induced osteogenesis better than a comparable hydroxyapatite scaffold. Calcite has been reported to remodel at a faster rate than natural or synthetic HA and tricalcium phosphate through in vitro osteoclast excavation experiments. Bone cement filled with calcite powder has also been made for biomedical use. Accordingly, the discovery herein of the ability to form calcite in vivo with implantable glass compositions, and to reduce, minimize, and/or eliminate HA formation, presents a significant advancement in treatment opportunities.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above compositions and methods without departing from the scope of the invention, it is intended that all matter contained in the above description and shown in the accompanying drawings shall be interpreted as illustrative and not in a limiting sense.

The invention claimed is:
1. A biocompatible composition for tissue repair or regeneration in mammals comprising:
   40 to 80 wt % B$_2$O$_3$;
   2.5 to 50 wt % CaO;
   one or more of MgO, SrO, and combinations thereof in a cumulative concentration of 5 to 40 wt %;
   one or more of Li$_2$O, Na$_2$O, K$_2$O, Rb$_2$O and combinations thereof;
   one or more director elements selected from the group consisting of Cu, Zn, Fe, Mn, Ba, Co, S, V, and/or Y in a cumulative concentration between 0.05 and 5 wt % to promote in vivo calcium compound formation of calcium carbonate or other calcium-containing materials other than hydroxyapatite;
   wherein upon direct application of the biocompatible composition to a mammalian host, calcium carbonate or other calcium-containing materials other than hydroxyapatite form upon bioreaction of the composition with bodily fluids;
wherein the composition is in a form of one or more of fibers, hollow fibers, tubes, ribbons, solid spheres, hollow spheres, particles, bonded particles, and combinations thereof assembled in a scaffold which has a porosity of between about 15 and about 90 vol % with at least about 75 vol % of pores being interconnected and suitable for application to a mammalian host such that it is exposed to the mammalian host's bodily fluids for tissue repair or regeneration in mammals; and
wherein the composition is not water soluble.

2. The biocompatible composition of claim 1 wherein said calcium carbonate or other calcium-containing materials other than hydroxyapatite that forms upon bioreaction of the composition with bodily fluids comprises calcite; and
wherein hydroxyapatite also forms upon bioreaction of the composition with bodily fluids.

3. The biocompatible composition of claim 1 wherein hydroxyapatite does not form upon bioreaction of the composition with bodily fluids.

4. The biocompatible composition of claim 3 wherein the director element is selected from the group consisting of Cu, Zn, Fe, Mn, Ba, Co, and/or S.

5. The biocompatible composition of claim 3 wherein the director element is selected from the group consisting of Cu, Mn, Ba, Co, and/or S.

6. The biocompatible composition of claim 3 wherein the director element is Zn and/or Fe.

7. The biocompatible composition of claim 1 comprising, approximately:
 40 to 80 wt % $B_2O_3$
 1 to 25 wt % $Na_2O$
 1 to 25% $K_2O$
 5 to 40 wt % CaO
 1 to 25 wt % MgO
 1 to 10 wt % $P_2O_5$
 said one or more director elements;
 said one or more of $Li_2O$, $Rb_2O$, $SiO_2$, $Al_2O_3$, and F.

8. The biocompatible composition of claim 1 consisting of approximately:
 40 to 80 wt % $B_2O_3$
 1 to 25 wt % $Na_2O$
 1 to 25% $K_2O$
 5 to 40 wt % CaO
 1 to 25 wt % MgO
 1 to 10 wt % $P_2O_5$
 and said one or more director elements,
 one or more of $Li_2O$, $Rb_2O$, $SiO_2$, $Al_2O_3$, and F.

9. The biocompatible composition of claim 1 comprising, approximately:
 40 to 80 wt % $B_2O_3$
 1 to 25 wt % $Na_2O$
 1 to 25% $K_2O$
 12 to 24 wt % CaO
 1 to 25 wt % MgO
 1 to 10 wt % $P_2O_5$
 0.1 to 2.5 wt % CuO.

10. The biocompatible composition of claim 1 comprising, approximately:
 40 to 80 wt % $B_2O_3$
 1 to 25 wt % $Na_2O$
 1 to 25% $K_2O$
 5 to 40 wt % CaO
 1 to 25 wt % MgO
 1 to 10 wt % $P_2O_5$
 0.1 to 2.5 wt % CuO.

11. The biocompatible composition of claim 1 comprising, approximately:
 40 to 80 wt % $B_2O_3$
 1 to 25 wt % $Na_2O$
 1 to 25% $K_2O$
 5 to 40 wt % CaO
 1 to 25 wt % MgO
 1 to 10 wt % $P_2O_5$
 0.1 to 2.5 wt % CuO
 0.1 to 2.5 wt % ZnO.

12. The biocompatible composition of claim 1 comprising, approximately:
 40 to 80 wt % $B_2O_3$
 1 to 25 wt % $Na_2O$
 1 to 25% $K_2O$
 5 to 40 wt % CaO
 1 to 25 wt % MgO
 1 to 10 wt % $P_2O_5$
 0.1 to 2.5 wt % CuO
 0.1 to 2.5 wt % ZnO
 0.1 to 2.5 wt % $Fe_2O_3$
 wherein the one or more director elements is supplied by said CuO, ZnO, and/or $Fe_2O_3$.

13. A biocompatible composition for tissue repair or regeneration in mammals comprising, approximately:
 40 to 80 wt % $B_2O_3$
 1 to 25 wt % $Na_2O$
 1 to 25% $K_2O$
 5 to 40 wt % CaO
 1 to 25 wt % MgO
 1 to 10 wt % $P_2O_5$
 one or more director elements selected from the group consisting of Cu, Zn, Fe, Mn, Ba, Co, S, V, and/or Y in a cumulative concentration between 0.05 and 5 wt % to promote in vivo calcium compound formation of calcium carbonate or other calcium-containing materials other than hydroxyapatite;
 optionally one or more of $Li_2O$, $Rb_2O$, $SiO_2$, $Al_2O_3$, and F;
 wherein the composition is in the form of a scaffold of glass fibers;
 wherein the scaffold has a porosity of between about 15 and about 90 vol % with at least about 75 vol % of pores being interconnected;
 wherein the glass fibers have lengths between about 2 and about 150 mm and a length:diameter aspect ratio of at least 5:1;
 wherein the composition is not water soluble.

14. The biocompatible composition of claim 3 wherein the composition comprises from 10 to 90 wt % of components having one composition and from 10 to 90 wt % of components of a different composition.

15. The biocompatible composition of claim 3 wherein the composition is in the form of fibers and spheres.

16. The biocompatible composition of claim 1 wherein the one or more director elements are Zn and Fe.

17. The biocompatible composition of claim 1 wherein the one or more director elements is Zn.

18. The biocompatible composition of claim 1 wherein the one or more director elements is Fe.

19. The composition of claim 1 comprising fibers having a diameter between 20 and 5000 microns.

20. The composition of claim 1 comprising fibers having a diameter between 100 and 300 microns.

21. The composition of claim 1 comprising particles having a particle size in the range of 150 to 300 microns.

* * * * *